US008129499B2

(12) United States Patent
Schultz-Cherry et al.

(10) Patent No.: US 8,129,499 B2
(45) Date of Patent: Mar. 6, 2012

(54) ANTIVIRAL PEPTIDES AGAINST INFLUENZA VIRUS

(75) Inventors: Stacey L. Schultz-Cherry, Germantown, TN (US); Curtis R. Brandt, Stoughton, WI (US); Jeremy C. Jones, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 248 days.

(21) Appl. No.: 12/484,853

(22) Filed: Jun. 15, 2009

(65) Prior Publication Data

US 2010/0041604 A1 Feb. 18, 2010

Related U.S. Application Data

(60) Provisional application No. 61/061,503, filed on Jun. 13, 2008.

(51) Int. Cl.

| | |
|---|---|
| ***A61K 38/00*** | (2006.01) |
| ***A61K 38/04*** | (2006.01) |
| ***A61K 39/145*** | (2006.01) |
| ***G01N 33/53*** | (2006.01) |

(52) U.S. Cl. ....... 530/326; 530/327; 435/7.1; 424/206.1

(58) Field of Classification Search ........................ None
See application file for complete search history.

(56) References Cited

U.S. PATENT DOCUMENTS

| | | |
|---|---|---|
| 5,624,898 A | 4/1997 | Frey, II |
| 6,180,603 B1 | 1/2001 | Frey, II |
| 6,313,093 B1 | 11/2001 | Frey, II |
| 2003/0077289 A1 | 4/2003 | Wang |
| 2005/0130884 A1 * | 6/2005 | Brandt et al. .................. 514/12 |
| 2005/0203024 A1 | 9/2005 | Brandt et al. |

FOREIGN PATENT DOCUMENTS

| | | |
|---|---|---|
| WO | 0033813 A1 | 6/2000 |
| WO | 0141782 A2 | 6/2001 |

OTHER PUBLICATIONS

Jones, et al., Inhibition of Influenza Virus Infection by a Novel Antiviral Peptide That Targets Viral Attachment to Cells, Journal of Virology, (2006) vol. 80(24), p. 11960-11967.
Schroeder and Lubke, in "The Peptides", vol. 1, Academic Press, New York, N. Y., pp. 2-136 (1965).
Wild et al., Proc. Natl. Acad. Sci. USA, 89: 10537-10541 (1992).
Rimsky et al., J Virol, 72: 986-993 (1998).
Reed and Muench, Am. J. Hyg., vol. 27, pp. 493-497 (1938).
Johansson, et al., Journal of Virology, 1989, vol. 63(3), p. 1239-1246.
Cianci, et al., Journal of Virology, 73(3):1785-94 (1999).
Lu, et al., "Immunity to influenza A H9N2 viruses induced by infection and vaccination," J. Virol., 2001, vol. 75(10), p. 4896-901.
Katz, et al., "Adjuvant activity of the heat-labile enterotoxin from enterotoxigenic *Escherichia coli* for oral administration of inactivated influenza virus vaccine," J. Infect. Dis., 1997, vol. 175(2), p. 352-63.
Rowe, et al., "Detection of antibody to avian influenza A (H5N1) virus in human serum by using a combination of serologic assays," J. Clin. Microbiol., 1999, vol. 37(4), p. 937-43.
International Search Report and Written Opinion from PCT/US09/47411, dated Oct. 8, 2009.
International Search Report and Written Opinion from PCT/US09/47412, dated Dec. 15, 2009.

* cited by examiner

*Primary Examiner* — Stacy B. Chen
(74) *Attorney, Agent, or Firm* — Armstrong Teasdale LLP

(57) ABSTRACT

The present disclosure generally relates to peptides having antiviral properties. More particularly, the invention relates to peptides exhibiting activity against influenza viruses, to pharmaceutical compositions comprising the peptides, and to methods of using the peptides to prevent and/or treat influenza viral infections.

11 Claims, 14 Drawing Sheets

FIG. 8

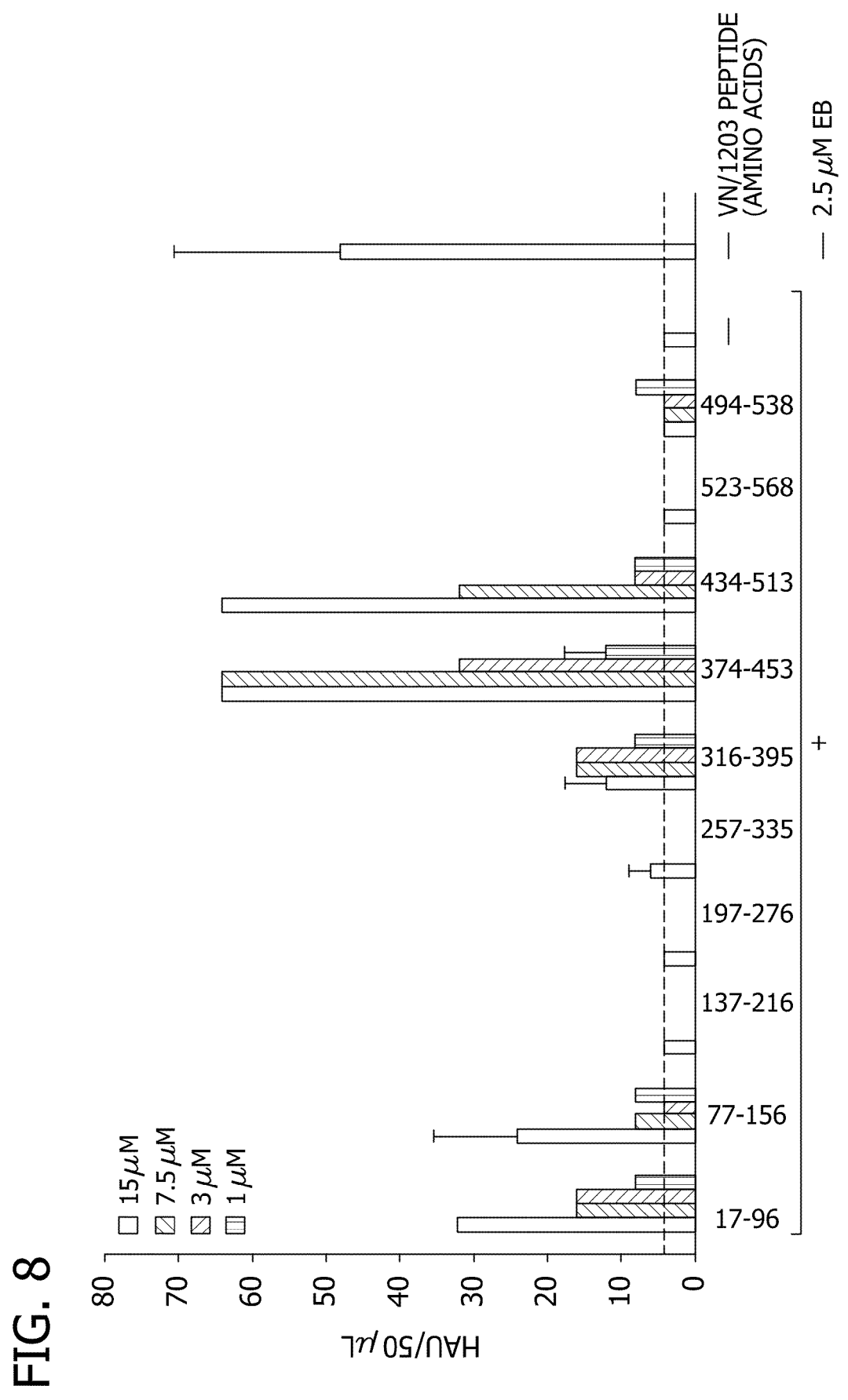

HAU/50 μL 80 70 60 50 40 30 20 10 0

15 μM
7.5 μM
3 μM
1 μM

VN/1203 PEPTIDE (AMINO ACIDS): 17-96, 77-156, 137-216, 197-276, 257-335, 316-395, 374-453, 434-513, 523-568, 494-538, —, —

2.5 μM EB: + (17-96 through —), —

| STRAIN | VIRUS |
|---|---|
| H5N1 | VN1203 374-453aa |
| H5N1 | HK/486 |
| H5N1 | VN1203 |
| H5N1 | HK/483 |
| H2N2 | SINGAPORE |
| H1N1 | PR/8 |
| H1N1 | NEWCAL |
| H1N1 | SWINE IND/88 |
| H1N1 | SWINE CAL/04 |
| H1N1 | SWINE CAL/05 |
| H1N1 | SWINE NY/19 |

50 60 70 80

| STRAIN | VIRUS |
|---|---|
| H5N1 | VN1203 374-453aa |
| H5N1 | HK/486 |
| H5N1 | VN1203 |
| H5N1 | HK/483 |
| H2N2 | SINGAPORE |
| H1N1 | PR/8 |
| H1N1 | NEWCAL |
| H1N1 | SWINE IND/88 |
| H1N1 | SWINE CAL/04 |
| H1N1 | SWINE CAL/05 |
| H1N1 | SWINE NY/19 |

SEQUENCE LISTING

```
<160> NUMBER OF SEQ ID NOS: 61

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Arg Lys Lys Ala Ala Val Ala Leu Leu Pro Ala Val Leu Leu Ala
1               5                   10                  15

Leu Leu Ala Pro
            20


<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Arg Lys Lys Ala Ala Val Ala Leu Leu Pro Ala Val Leu Leu Ala
1               5                   10                  15

Leu Leu Ala


<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Arg Lys Lys Ala Ala Val Ala Leu Leu Pro Ala Val Leu Leu Ala
1               5                   10                  15

Leu Leu


<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Arg Lys Lys Ala Ala Val Ala Leu Leu Pro Ala Val Leu Leu Ala
1               5                   10                  15

Leu


<210> SEQ ID NO 5
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 5

Arg Arg Lys Lys Ala Ala Val Ala Leu Leu Pro Ala Val Leu Leu Ala
1               5                   10                  15


<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Arg Lys Lys Ala Ala Val Ala Leu Leu Pro Ala Val Leu Leu
1               5                   10                  15


<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Arg Lys Lys Ala Ala Val Ala Leu Leu Pro Ala Val Leu
1               5                   10


<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Arg Lys Lys Ala Ala Val Ala Leu Leu Pro Ala Val
1               5                   10


<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Arg Lys Lys Ala Ala Val Ala Leu Leu Pro Ala
1               5                   10


<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Arg Lys Lys Ala Ala Val Ala Leu Leu Pro
1               5                   10
```

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Arg Arg Lys Lys Ala Ala Val Ala Leu Leu
1 5 10

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Arg Arg Lys Lys Ala Ala Val Ala Leu
1 5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Arg Arg Lys Lys Ala Ala Val Ala
1 5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Arg Arg Lys Lys Ala Ala Val
1 5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Arg Arg Lys Lys Ala Ala
1 5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Arg Arg Lys Lys Ala
1 5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Arg Arg Lys Lys
1

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Arg Arg Lys Lys Ala Val Ala Leu Leu Pro Ala Val Leu Leu Ala Leu
1 5 10 15

Leu Ala Pro

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Arg Arg Lys Lys Val Ala Leu Leu Pro Ala Val Leu Leu Ala Leu Leu
1 5 10 15

Ala Pro

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Arg Arg Lys Lys Ala Leu Leu Pro Ala Val Leu Leu Ala Leu Leu Ala
1 5 10 15

Pro

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Arg Arg Lys Lys Leu Leu Pro Ala Val Leu Leu Ala Leu Leu Ala Pro
1 5 10 15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

```
Arg Arg Lys Lys Leu Pro Ala Val Leu Leu Ala Leu Leu Ala Pro
1               5                   10                  15
```

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

```
Arg Arg Lys Lys Val Leu Leu Ala Leu Leu Ala Pro
1               5                   10
```

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

```
Arg Arg Lys Lys Leu Leu Ala Leu Leu Ala Pro
1               5                   10
```

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

```
Arg Arg Lys Lys Ala Leu Leu Ala Pro
1               5
```

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

```
Arg Arg Lys Lys Leu Leu Ala Pro
1               5
```

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

```
Arg Arg Lys Lys Leu Ala Pro
1               5


<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Arg Lys Lys Ala Pro
1               5


<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Arg Lys Lys Pro
1               5


<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Arg Lys Lys Ala Ala Leu Leu Val Leu Ala Ala Leu Ala Val Leu
1               5                   10                  15

Ala


<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Arg Lys Lys Leu Ala Ala Leu Pro Leu Val Leu Ala Ala Pro Leu
1               5                   10                  15

Ala Val Leu Ala
            20


<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Arg Lys Lys Val Ala Leu Leu Ala Val Leu Leu Ala Leu Leu Ala
1               5                   10                  15
```

```
<210> SEQ ID NO 33
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: Region may encompass 0 or 3-10 charged amino
      acids
<220> FEATURE:
<221> NAME/KEY: MOD_RES
<222> LOCATION: (26)..(35)
<223> OTHER INFORMATION: Region may encompass 0 or 3-10 charged amino
      acids
<220> FEATURE:
<223> OTHER INFORMATION: See specification as filed for detailed
      description of substitutions and preferred embodiments

<400> SEQUENCE: 33

Xaa Xaa Xaa Xaa Xaa Xaa Xaa Xaa Xaa Xaa Ala Ala Val Ala Leu Leu
1               5                   10                  15

Pro Ala Val Leu Leu Ala Leu Leu Ala Xaa Xaa Xaa Xaa Xaa Xaa Xaa
            20                  25                  30

Xaa Xaa Xaa
        35


<210> SEQ ID NO 34
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: Region may encompass 0 or 3-10 charged amino
      acids
<220> FEATURE:
<221> NAME/KEY: MOD_RES
<222> LOCATION: (25)..(34)
<223> OTHER INFORMATION: Region may encompass 0 or 3-10 charged amino
      acids
<220> FEATURE:
<223> OTHER INFORMATION: See specification as filed for detailed
      description of substitutions and preferred embodiments

<400> SEQUENCE: 34

Xaa Xaa Xaa Xaa Xaa Xaa Xaa Xaa Xaa Xaa Ala Ala Val Ala Leu Leu
1               5                   10                  15

Pro Ala Val Leu Leu Ala Leu Leu Xaa Xaa Xaa Xaa Xaa Xaa Xaa Xaa
            20                  25                  30

Xaa Xaa


<210> SEQ ID NO 35
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: Region may encompass 0 or 3-10 charged amino
      acids
<220> FEATURE:
<221> NAME/KEY: MOD_RES
<222> LOCATION: (24)..(33)
```

```
<223> OTHER INFORMATION: Region may encompass 0 or 3-10 charged amino
      acids
<220> FEATURE:
<223> OTHER INFORMATION: See specification as filed for detailed
      description of substitutions and preferred embodiments

<400> SEQUENCE: 35

Xaa Xaa Xaa Xaa Xaa Xaa Xaa Xaa Xaa Xaa Ala Ala Val Ala Leu Leu
1               5                   10                  15

Pro Ala Val Leu Leu Ala Leu Xaa Xaa Xaa Xaa Xaa Xaa Xaa Xaa Xaa
            20                  25                  30

Xaa


<210> SEQ ID NO 36
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: Region may encompass 0 or 3-10 charged amino
      acids
<220> FEATURE:
<221> NAME/KEY: MOD_RES
<222> LOCATION: (23)..(32)
<223> OTHER INFORMATION: Region may encompass 0 or 3-10 charged amino
      acids
<220> FEATURE:
<223> OTHER INFORMATION: See specification as filed for detailed
      description of substitutions and preferred embodiments

<400> SEQUENCE: 36

Xaa Xaa Xaa Xaa Xaa Xaa Xaa Xaa Xaa Xaa Ala Ala Val Ala Leu Leu
1               5                   10                  15

Pro Ala Val Leu Leu Ala Xaa Xaa Xaa Xaa Xaa Xaa Xaa Xaa Xaa Xaa
            20                  25                  30


<210> SEQ ID NO 37
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: Region may encompass 0 or 3-10 charged amino
      acids
<220> FEATURE:
<221> NAME/KEY: MOD_RES
<222> LOCATION: (26)..(35)
<223> OTHER INFORMATION: Region may encompass 0 or 3-10 charged amino
      acids
<220> FEATURE:
<223> OTHER INFORMATION: See specification as filed for detailed
      description of substitutions and preferred embodiments

<400> SEQUENCE: 37

Xaa Xaa Xaa Xaa Xaa Xaa Xaa Xaa Xaa Xaa Ala Val Ala Leu Leu Pro
1               5                   10                  15

Ala Val Leu Leu Ala Leu Leu Ala Pro Xaa Xaa Xaa Xaa Xaa Xaa Xaa
            20                  25                  30

Xaa Xaa Xaa
        35
```

<210> SEQ ID NO 38
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(10)
<223> OTHER INFORMATION: Region may encompass 0 or 3-10 charged amino acids
<220> FEATURE:
<221> NAME/KEY: MOD_RES
<222> LOCATION: (25)..(34)
<223> OTHER INFORMATION: Region may encompass 0 or 3-10 charged amino acids
<220> FEATURE:
<223> OTHER INFORMATION: See specification as filed for detailed description of substitutions and preferred embodiments

<400> SEQUENCE: 38

```
Xaa Xaa Xaa Xaa Xaa Xaa Xaa Xaa Xaa Xaa Val Ala Leu Leu Pro Ala
1               5                   10                  15

Val Leu Leu Ala Leu Leu Ala Pro Xaa Xaa Xaa Xaa Xaa Xaa Xaa Xaa
            20                  25                  30

Xaa Xaa
```

<210> SEQ ID NO 39
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(10)
<223> OTHER INFORMATION: Region may encompass 0 or 3-10 charged amino acids
<220> FEATURE:
<221> NAME/KEY: MOD_RES
<222> LOCATION: (24)..(33)
<223> OTHER INFORMATION: Region may encompass 0 or 3-10 charged amino acids
<220> FEATURE:
<223> OTHER INFORMATION: See specification as filed for detailed description of substitutions and preferred embodiments

<400> SEQUENCE: 39

```
Xaa Xaa Xaa Xaa Xaa Xaa Xaa Xaa Xaa Xaa Ala Leu Leu Pro Ala Val
1               5                   10                  15

Leu Leu Ala Leu Leu Ala Pro Xaa Xaa Xaa Xaa Xaa Xaa Xaa Xaa Xaa
            20                  25                  30

Xaa
```

<210> SEQ ID NO 40
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(10)
<223> OTHER INFORMATION: Region may encompass 0 or 3-10 charged amino acids
<220> FEATURE:
<221> NAME/KEY: MOD_RES
<222> LOCATION: (23)..(32)
<223> OTHER INFORMATION: Region may encompass 0 or 3-10 charged amino

```
      acids
<220> FEATURE:
<223> OTHER INFORMATION: See specification as filed for detailed
      description of substitutions and preferred embodiments

<400> SEQUENCE: 40

Xaa Xaa Xaa Xaa Xaa Xaa Xaa Xaa Xaa Xaa Leu Leu Pro Ala Val Leu
1               5                   10                  15

Leu Ala Leu Leu Ala Pro Xaa Xaa Xaa Xaa Xaa Xaa Xaa Xaa Xaa Xaa
            20                  25                  30


<210> SEQ ID NO 41
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: Region may encompass 0 or 3-10 charged amino
      acids
<220> FEATURE:
<221> NAME/KEY: MOD_RES
<222> LOCATION: (22)..(31)
<223> OTHER INFORMATION: Region may encompass 0 or 3-10 charged amino
      acids
<220> FEATURE:
<223> OTHER INFORMATION: See specification as filed for detailed
      description of substitutions and preferred embodiments

<400> SEQUENCE: 41

Xaa Xaa Xaa Xaa Xaa Xaa Xaa Xaa Xaa Xaa Leu Pro Ala Val Leu Leu
1               5                   10                  15

Ala Leu Leu Ala Pro Xaa Xaa Xaa Xaa Xaa Xaa Xaa Xaa Xaa Xaa
            20                  25                  30


<210> SEQ ID NO 42
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: Region may encompass 0 or 3-10 charged amino
      acids
<220> FEATURE:
<221> NAME/KEY: MOD_RES
<222> LOCATION: (19)..(28)
<223> OTHER INFORMATION: Region may encompass 0 or 3-10 charged amino
      acids
<220> FEATURE:
<223> OTHER INFORMATION: See specification as filed for detailed
      description of substitutions and preferred embodiments

<400> SEQUENCE: 42

Xaa Xaa Xaa Xaa Xaa Xaa Xaa Xaa Xaa Xaa Val Leu Leu Ala Leu Leu
1               5                   10                  15

Ala Pro Xaa Xaa Xaa Xaa Xaa Xaa Xaa Xaa Xaa Xaa
            20                  25


<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 43

```
Arg Arg Lys Lys Ala Ala Val Ala Leu Leu Ala Val Leu Leu Ala Leu
1               5                   10                  15

Leu Ala
```

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

```
Arg Arg Lys Lys Leu Leu Ala Val Leu Leu Ala Leu Leu Ala
1               5                   10
```

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

```
Arg Arg Lys Lys Leu Ala Val Leu Leu Ala Leu Leu Ala
1               5                   10
```

<210> SEQ ID NO 46
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(10)
<223> OTHER INFORMATION: Region may encompass 0 or 3-10 charged amino acids
<220> FEATURE:
<221> NAME/KEY: MOD_RES
<222> LOCATION: (25)..(34)
<223> OTHER INFORMATION: Region may encompass 0 or 3-10 charged amino acids
<220> FEATURE:
<223> OTHER INFORMATION: See specification as filed for detailed description of substitutions and preferred embodiments

<400> SEQUENCE: 46

```
Xaa Xaa Xaa Xaa Xaa Xaa Xaa Xaa Xaa Xaa Ala Ala Val Ala Leu Leu
1               5                   10                  15

Ala Val Leu Leu Ala Leu Leu Ala Xaa Xaa Xaa Xaa Xaa Xaa Xaa Xaa
            20                  25                  30

Xaa Xaa
```

<210> SEQ ID NO 47
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(10)

```
<223> OTHER INFORMATION: Region may encompass 0 or 3-10 charged amino
      acids
<220> FEATURE:
<221> NAME/KEY: MOD_RES
<222> LOCATION: (21)..(30)
<223> OTHER INFORMATION: Region may encompass 0 or 3-10 charged amino
      acids
<220> FEATURE:
<223> OTHER INFORMATION: See specification as filed for detailed
      description of substitutions and preferred embodiments

<400> SEQUENCE: 47

Xaa Xaa Xaa Xaa Xaa Xaa Xaa Xaa Xaa Xaa Leu Leu Ala Val Leu Leu
1               5                   10                  15

Ala Leu Leu Ala Xaa Xaa Xaa Xaa Xaa Xaa Xaa Xaa Xaa Xaa
            20                  25                  30


<210> SEQ ID NO 48
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: Region may encompass 0 or 3-10 charged amino
      acids
<220> FEATURE:
<221> NAME/KEY: MOD_RES
<222> LOCATION: (20)..(29)
<223> OTHER INFORMATION: Region may encompass 0 or 3-10 charged amino
      acids
<220> FEATURE:
<223> OTHER INFORMATION: See specification as filed for detailed
      description of substitutions and preferred embodiments

<400> SEQUENCE: 48

Xaa Xaa Xaa Xaa Xaa Xaa Xaa Xaa Xaa Xaa Leu Ala Val Leu Leu Ala
1               5                   10                  15

Leu Leu Ala Xaa Xaa Xaa Xaa Xaa Xaa Xaa Xaa Xaa Xaa
            20                  25


<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Arg Lys Lys Ala Ala Ala Ala Ala Ala Ala Ala Ala
1               5                   10


<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Lys Lys Leu Ala Val Leu Leu Ala Leu Leu Ala
1               5                   10


<210> SEQ ID NO 51
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Lys Ala Val Leu Leu Ala Leu Leu Ala
1               5                   10


<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Leu Ala Val Leu Leu Ala Leu Leu Ala
1               5                   10


<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Lys Lys Leu Ala Val Leu Leu Ala Leu Leu Ala
1               5                   10


<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Glu Glu Asp Asp Leu Ala Val Leu Leu Ala Leu Leu Ala
1               5                   10


<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Arg Lys Lys Leu Ala Val Ala Ala Ala Leu Leu Ala
1               5                   10


<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Arg Lys Lys Leu Ala Val Leu Leu Ala Ala Ala Ala
1               5                   10
```

<210> SEQ ID NO 57
<211> LENGTH: 29
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(10)
<223> OTHER INFORMATION: Region may encompass 0 or 3-10 charged amino acids
<220> FEATURE:
<221> NAME/KEY: MOD_RES
<222> LOCATION: (20)..(29)
<223> OTHER INFORMATION: Region may encompass 0 or 3-10 charged amino acids
<220> FEATURE:
<223> OTHER INFORMATION: See specification as filed for detailed description of substitutions and preferred embodiments

<400> SEQUENCE: 57

```
Xaa Xaa Xaa Xaa Xaa Xaa Xaa Xaa Xaa Xaa Ala Ala Ala Ala Ala Ala
1               5                   10                  15

Ala Ala Ala Xaa Xaa Xaa Xaa Xaa Xaa Xaa Xaa Xaa Xaa
            20                  25
```

<210> SEQ ID NO 58
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(10)
<223> OTHER INFORMATION: Region may encompass 0 or 3-10 charged amino acids
<220> FEATURE:
<221> NAME/KEY: MOD_RES
<222> LOCATION: (23)..(32)
<223> OTHER INFORMATION: Region may encompass 0 or 3-10 charged amino acids
<220> FEATURE:
<223> OTHER INFORMATION: See specification as filed for detailed description of substitutions and preferred embodiments

<400> SEQUENCE: 58

```
Xaa Xaa Xaa Xaa Xaa Xaa Xaa Xaa Xaa Xaa Arg Lys Lys Leu Ala Val
1               5                   10                  15

Leu Leu Ala Leu Leu Ala Xaa Xaa Xaa Xaa Xaa Xaa Xaa Xaa Xaa Xaa
            20                  25                  30
```

<210> SEQ ID NO 59
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(10)
<223> OTHER INFORMATION: Region may encompass 0 or 3-10 charged amino acids
<220> FEATURE:
<221> NAME/KEY: MOD_RES
<222> LOCATION: (21)..(30)
<223> OTHER INFORMATION: Region may encompass 0 or 3-10 charged amino acids
<220> FEATURE:

-continued

```
<223> OTHER INFORMATION: See specification as filed for detailed
      description of substitutions and preferred embodiments

<400> SEQUENCE: 59

Xaa Xaa Xaa Xaa Xaa Xaa Xaa Xaa Xaa Xaa Arg Lys Ala Val Leu Leu
1               5                   10                  15

Ala Leu Leu Ala Xaa Xaa Xaa Xaa Xaa Xaa Xaa Xaa Xaa Xaa
            20                  25                  30


<210> SEQ ID NO 60
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: Region may encompass 0 or 3-10 charged amino
      acids
<220> FEATURE:
<221> NAME/KEY: MOD_RES
<222> LOCATION: (21)..(30)
<223> OTHER INFORMATION: Region may encompass 0 or 3-10 charged amino
      acids
<220> FEATURE:
<223> OTHER INFORMATION: See specification as filed for detailed
      description of substitutions and preferred embodiments

<400> SEQUENCE: 60

Xaa Xaa Xaa Xaa Xaa Xaa Xaa Xaa Xaa Xaa Lys Leu Ala Val Leu Leu
1               5                   10                  15

Ala Leu Leu Ala Xaa Xaa Xaa Xaa Xaa Xaa Xaa Xaa Xaa Xaa
            20                  25                  30


<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Glu Glu Asp Asp
1
```

ANTIVIRAL PEPTIDES AGAINST INFLUENZA VIRUS

CROSS-REFERENCE TO RELATED APPLICATIONS

This application claims priority from U.S. Provisional Patent Application Ser. No. 61/061,503, filed Jun. 13, 2008, which is herein incorporated by reference in its entirety.

STATEMENT REGARDING FEDERALLY SPONSORED RESEARCH OR DEVELOPMENT

This invention was made with government support under AI052049 and EY007336 awarded by the National Institutes of Health. The government has certain rights in the invention.

REFERENCE TO A SEQUENCE LISTING

This application includes a Sequence Listing. A paper copy and a computer readable copy of the Sequence Listing are being submitted concurrently herewith. The information contained in the Sequence Listing is herein incorporated by reference in its entirety.

BACKGROUND OF THE DISCLOSURE

The present disclosure generally relates to peptides having antiviral properties. More particularly, the invention relates to peptides exhibiting activity against influenza viruses, to pharmaceutical compositions comprising the peptides, and to methods of using the peptides to prevent and/or treat influenza viral infections.

Outbreaks of influenza A virus continue to cause widespread morbidity and mortality worldwide. In the United States alone, an estimated 5 to 20% of the population is infected by influenza A virus annually, causing approximately 200,000 hospitalizations and 36,000 deaths. The establishment of comprehensive vaccination policies has been an effective measure to limit influenza morbidity. However, the frequent genetic drifting of the virus requires yearly reformulation of the vaccine, potentially leading to a mismatch between the viral strain present in the vaccine and that circulating. Thus, antiviral therapies against influenza virus are important tools to limit both disease severity as well as transmission.

Currently, there are two classes of influenza antivirals approved for widespread distribution, including adamantine derivatives (e.g., amantadine and rimantadine), and neuraminidase inhibitors. The adamantines target the viral M2 protein, and prevent the virus from uncoating and releasing its genetic material into the cell. In contrast, the neuraminidase inhibitors (NAIs), block the enzymatic activity of the neuraminidase (NA) surface protein, and halt viral egress. Unfortunately, there are increasing reports of emerging viruses resistant to both classes of antivirals. Due to large scale resistance, the Centers for Disease Control and Prevention and others have recommended against the use of the adamantanes for treatment or prophylaxis of influenza viruses. Thus, there is an urgent need to identify and characterize new antiviral drugs for both treatment and control of influenza.

In recent years, various peptides having activity against viruses have been disclosed. For example, a 20-amino acid peptide derived from the fibroblast growth factor 4 (FGF-4) signal sequence and designated entry blocker (EB), has been shown to display significant broad-spectrum activity against influenza viruses in vitro and in vivo. The EB peptide has been described in Jones, et al., "Inhibition of Influenza Virus Infection by a Novel Antiviral Peptide That Targets Viral Attachment to Cells, *Journal of Virology*, (2006) Vol. 80(24), p. 11960-11967, and in U.S. patent Application Publ. No. 2005/0130884 to Brandt, et al. and in U.S. patent Application Publ. No. 2005/0203024 also to Brandt, et al. Specifically, it has been demonstrated that in vitro, EB inhibits virus replication at concentrations of 10 μM or greater. In BALB/c mice, EB prevented clinical signs of H5N1 influenza virus infection and increased survival when administered pre- or post-infection. It has also been established that EB inhibited influenza virus attachment to cells potentially through a direct binding interaction with the viral hemagglutinin (HA) protein. However, the precise mechanism of binding has not been determined.

It has now been discovered that certain derivatives of the EB peptide exhibit antiviral activity against influenza viruses. Advantageously, the antiviral peptides of the present disclosure exhibit antiviral activity that is comparable to or better than that of EB. Additionally, because the peptides are shorter in length than EB and other known antiviral peptides, the production costs of the peptides are also decreased.

SUMMARY OF THE DISCLOSURE

The present disclosure generally relates to peptides having antiviral properties. More particularly, the invention relates to peptides exhibiting activity against influenza viruses, to pharmaceutical compositions comprising the peptides, and to methods of using the peptides to prevent and/or treat influenza viral infections.

In one aspect, the present disclosure is directed to an antiviral peptide selected from the group consisting of SEQ ID NOs: 2-3, SEQ ID NO: 5, SEQ ID NOs: 18-19, SEQ ID NOs: 21-23, SEQ ID NO: 30, SEQ ID NOs: 32-34, SEQ ID NOs: 36-38, SEQ ID NOs: 40-51, and SEQ ID NOs: 57-59.

In another aspect, the present disclosure is directed to a composition comprising one or more peptide selected from the group consisting of SEQ ID NOs: 2-3, SEQ ID NO: 5, SEQ ID NOs: 18-19, SEQ ID NOs: 21-23, SEQ ID NO: 30, SEQ ID NOs: 32-34, SEQ ID NOs: 36-38, SEQ ID NOs: 40-51, and SEQ ID NOs: 57-59, and a pharmaceutically acceptable carrier.

In still another aspect, the present disclosure is directed to a composition comprising a derivative of a peptide having SEQ ID NO: 1, wherein the derivative comprises from 12 to 19 amino acids and displays significant antiviral activity against influenza viruses.

In another aspect, the present disclosure is directed to a method of treating or preventing a viral respiratory infection in a mammal, the method comprising administering to the mammal an effective amount of an antiviral peptide selected from the group consisting of: a) SEQ ID NOs: 2-3, SEQ ID NO: 5, SEQ ID NOs: 18-19, SEQ ID NOs: 21-23, SEQ ID NO: 30, SEQ ID NOs: 32-34, SEQ ID NOs: 36-38, SEQ ID NOs: 40-51, and SEQ ID NOs: 57-59; b) a derivative of a peptide having SEQ ID NO: 1, wherein the derivative comprises from 12 to 19 amino acids and displays significant antiviral activity against influenza viruses; and c) combinations thereof.

BRIEF DESCRIPTION OF THE DRAWINGS

FIG. 8 is a graph showing the results of an EB peptide inhibition assay performed by incubating concentrations of 1 μM, 3 μM 7.5 μM or 15 μM of various overlapping VN/1203 HA peptides with 2.5 μM of the EB peptide, and evaluating the ability of the EB peptide to inhibit the activity of PR/8 virus, as discussed in Example 7. All measures were performed in duplicate. The dotted line indicates the normal inhibition of PR/8 by 2.5 μM of the EB peptide. The amino acid residues for the overlapping HA peptides tested are shown along the x-axis.

FIG. 9 shows the amino acid alignment of amino acids 374-453 of VN/1203 HA protein with various additional influenza A viruses, as discussed in Example 7. Shading and dots indicate similar (light shading) and identical (dark shading) residues. The influenza viruses tested were: A/Vietnam/1203/04 (VN/1203); A/HongKong/486/97 (HK/486); A/HongKong/483/97 (HK/483); A/Singapore/1/57 (SINGAPORE); A/PuertoRico/8/34 (PR/8); A/NewCaledonia/20/99 (NEWCAL); A/swine/Indiana/1726/88 (SWINE IND/88); A/California/04/09 (SWINE CAL/04); A/California/05/09 (SWINE CAL/05); and A/NewYork/19/09 (SWINE NY/19).

DETAILED DESCRIPTION OF THE DISCLOSURE

Figure 1A:
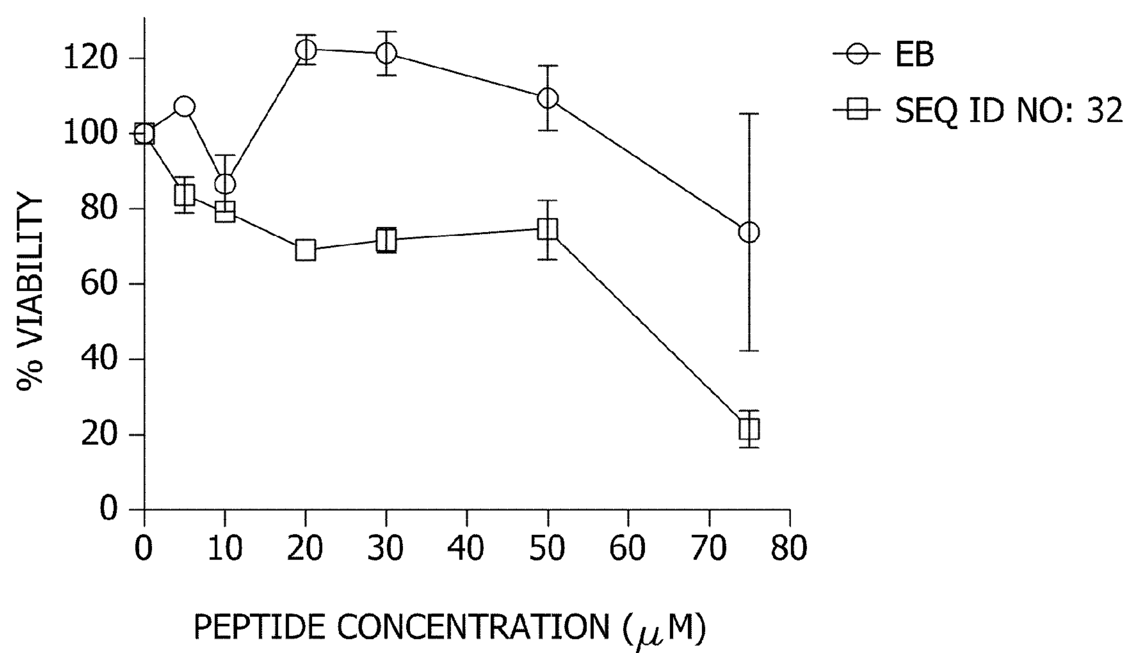
FIG. 1A is a graph showing the cytotoxic effects of EB (○) and the peptide SEQ ID NO: 32 (□), as discussed in Example 2. Data are presented as the mean value±standard deviation of triplicate measurements.

The present disclosure generally relates to peptides having antiviral properties. More particularly, the invention relates to peptides exhibiting antiviral activity against influenza viruses, to pharmaceutical compositions comprising the peptides, and to methods of using the peptides to prevent and/or treat influenza viral infections.

Definitions

Pharmaceutically acceptable carrier: An acceptable vehicle for administering antiviral peptides to mammals comprising one or more non-toxic excipients which do not react with or reduce the effectiveness of the pharmacologically active antiviral peptide contained therein.

Solubility tag: A short peptide sequence comprised of charged amino acids which, when attached to a terminal residue of a longer insoluble peptide sequence, will improve solubility in an aqueous medium. In some embodiments the charged amino acids of the solubility tags are exclusively positively charged amino acids, including, but not limited to, ornithine, lysine, and arginine. Solubility tags may be 2 to 24 amino acids long or longer, and typically can be 4, 5, 6, 7, 8, 9, 10, 11, 12, 13, 14, 15, or 16 amino acids long. A solubility tag may be attached to either terminus or both termini of the longer insoluble peptide.

The following standard one letter abbreviated names for the amino acids are used hereinafter: alanine (A), lysine (K), leucine (L), proline (P), arginine (R), valine (V), glutamic acid (E), and aspartic acid (D). All amino acid sequences in this application are depicted using standard nomenclature, with the left most amino acid residue at the end of each sequence being the amino-terminal residue and the residue at the right end of each sequence being the carboxyl-terminal residue. The amino acids of the peptides described herein may be either levo ("l") amino acids or dextro ("d") amino acids. Any of the peptides described herein can have peptide backbones made up of d amino acids.

The present disclosure is directed to novel antiviral peptides which are derivatives of the EB peptide. EB is a 20-amino acid antiviral peptide derived from a fibroblast growth factor, which contains sixteen hydrophobic amino acids, with a highly charged tetrapeptide (RRKK) (SEQ ID NO: 17) added to the N-terminus to enhance solubility. EB has the sequence RRKKAAVALLPAVLLALLAP (SEQ ID NO: 1). EB has previously been demonstrated to display antiviral activity against influenza viruses by inhibiting virus binding to host cells. See Jones, et al., *Journal of Virology*, (2006) Vol. 80(24), pp. 11960-11967.

It has now been discovered that certain derivatives of EB display antiviral activity that is comparable to the antiviral activity of EB. More particularly, it has been discovered that up to 4 amino acids can be deleted from the C-terminus of the EB peptide without significant loss of anti-viral activity. Additionally, up to 8 amino acids can be deleted from the N-terminus of the EB peptide (while retaining the R-R-K-K (SEQ ID NO: 17) solubility tag) without significant loss of anti-viral activity. It has also been discovered that the proline residues may be removed from various antiviral peptides of the present disclosure with little to no loss of antiviral activity.

Other modifications are also within the scope of the instant disclosure. The antiviral peptides of the present disclosure typically comprise from about 12 to about 19 residues, and exhibit a broad spectrum of antiviral activity against influenza virus.

Exemplary antiviral peptides derived from EB are described below in Table 1. SEQ. ID. NOS: 2-5 and 18-23 are based on the EB peptide sequence, but have had individual amino acids (anywhere from one to eight amino acids) deleted from either the N- or -C terminus of EB, while retaining the R-R-K-K (SEQ ID NO: 17) solubility tag. SEQ. ID. NO: 30 was obtained by retaining the R-R-K-K (SEQ ID NO: 17) solubility tag, deleting two proline residues and a leucine residue from the EB peptide, and randomly rearranging the remaining amino acids from the EB sequence. SEQ. ID. NO: 43 was obtained by deleting the two proline residues from the EB sequence. SEQ. ID. NOs: 32, 44, and 45 are similar to SEQ. ID. NOs: 19, 21, and 22, respectively, except both proline residues have been deleted. SEQ ID NO: 49 was obtained by retaining the RRKK (SEQ ID NO: 17) solubility tag and substituting alanine residues for the remaining amino acid residues in SEQ ID NO: 45. SEQ ID NOs: 50 and 52 are similar to SEQ ID NO: 45, except the R or RRK, respectively, have been removed from the N-terminus. SEQ ID NO: 51 was obtained by removing an R, K, and L from SEQ ID NO: 45.

TABLE 1

| Peptide | Sequence | Purpose |
|---|---|---|
| SEQ. ID. NO: 2 | RRKKAAVALLPAVLLALLA | -1C-terminus of EB |
| SEQ. ID. NO: 3 | RRKKAAVALLPAVLLALL | -2C-terminus of EB |
| SEQ. ID. NO: 4 | RRKKAAVALLPAVLLAL | -3C-terminus of EB |
| SEQ. ID. NO: 5 | RRKKAAVALLPAVLLA | -4C-terminus of EB |
| SEQ. ID. NO: 18 | RRKKAVALLPAVLLALLAP | -1N-terminus of EB |
| SEQ. ID. NO: 19 | RRKKVALLPAVLLALLAP | -2N-terminus of EB |
| SEQ. ID. NO: 20 | RRKKALLPAVLLALLAP | -3N-terminus of EB |
| SEQ. ID. NO: 21 | RRKKLLPAVLLALLAP | -4N-terminus of EB |
| SEQ. ID. NO: 22 | RRKKLPAVLLALLAP | -5N-terminus of EB |
| SEQ. ID. NO: 23 | RRKKVLLALLAP | -8N-terminus of EB |
| SEQ. ID. NO: 30 | RRKKAALLVLAALAVLA | Scrambled EB; 2 prolines and 1 leucine deleted |
| SEQ. ID. NO: 32 | RRKKVALLAVLLALLA | 2 proline residues removed from SEQ. ID. NO: 19. |
| SEQ. ID. NO: 43 | RRKKAAVALLAVLLALLA | 2 proline residues removed from EB |
| SEQ. ID. NO: 44 | RRKKLLAVLLALLA | 2 proline residues removed from SEQ. ID. NO: 21 |
| SEQ. ID. NO: 45 | RRKKLAVLLALLA | 2 proline residues removed from SEQ. ID. NO: 22 |
| SEQ. ID. NO: 49 | RRKKAAAAAAAAA | A substitution |
| SEQ. ID. NO: 50 | RKKLAVLLALLA | R removed from N-terminus of SEQ ID NO: 45 |
| SEQ. ID. NO: 51 | RKAVLLALLA | RK and L removed from SEQ. ID. NO: 45 |
| SEQ. ID. NO: 52 | KLAVLLALLA | RRKK removed from N-terminus of SEQ ID NO: 45 |

As can be seen from Table 1, with the exception of SEQ ID NO: 49, the exemplary antiviral peptides listed therein all contain di-leucine repeat regions. Without wishing to be bound to any particular theory, it is believed that in some instances, the presence of di-leucine repeat regions in the peptides may contribute to the anti-viral activity of the peptides.

The SEQ ID NO: 2-5, 18-23, 30, 32, and 43-49 antiviral peptides listed in Table 1 all include a solubility tag (RRKK) (SEQ ID NO: 17) covalently attached to a sequence of hydrophobic amino acids. In addition to the peptides listed in Table 1, antiviral peptides of the present disclosure may also comprise other solubility tags covalently attached thereto. Additional exemplary antiviral peptides are set forth in Table 2.

TABLE 2

| Peptide | Sequence |
|---|---|
| SEQ ID NO: 33 | $(X1)_n$-A-A-V-A-L-L-P-A-V-L-L-A-L-L-A-$(X2)_m$ |
| SEQ ID NO: 34 | $(X1)_n$-A-A-V-A-L-L-P-A-V-L-L-A-L-L-$(X2)_m$ |
| SEQ ID NO: 35 | $(X1)_n$-A-A-V-A-L-L-P-A-V-L-L-A-L-$(X2)_m$ |
| SEQ ID NO: 36 | $(X1)_n$-A-A-V-A-L-L-P-A-V-L-L-A-$(X2)_m$ |
| SEQ ID NO: 37 | $(X1)_n$-A-V-A-L-L-P-A-V-L-L-A-L-L-A-P-$(X2)_m$ |
| SEQ ID NO: 38 | $(X1)_n$-V-A-L-L-P-A-V-L-L-A-L-L-A-P-$(X2)_m$ |
| SEQ ID NO: 39 | $(X1)_n$-A-L-L-P-A-V-L-L-A-L-L-A-P-$(X2)_m$ |
| SEQ ID NO: 40 | $(X1)_n$-L-L-P-A-V-L-L-A-L-L-A-P-$(X2)_m$ |
| SEQ ID NO: 41 | $(X1)_n$-L-P-A-V-L-L-A-L-L-A-P-$(X2)_m$ |
| SEQ ID NO: 42 | $(X1)_n$-V-L-L-A-L-L-A-P-$(X2)_m$ |
| SEQ ID NO: 46 | $(X1)_n$-A-A-V-A-L-L-A-V-L-L-A-L-L-A-$(X2)_m$ |
| SEQ ID NO: 47 | $(X1)_n$-L-L-A-V-L-L-A-L-L-A-$(X2)_m$ |
| SEQ ID NO: 48 | $(X1)_n$-L-A-V-L-L-A-L-L-A-$(X2)_m$ |
| SEQ ID NO: 57 | $(X1)_n$-A-A-A-A-A-A-A-A-A-$(X2)_m$ |
| SEQ ID NO: 58 | $(X1)_n$-R-K-K-L-A-V-L-L-A-L-L-A-$(X2)_m$ |
| SEQ ID NO: 59 | $(X1)_n$-R-K-A-V-L-L-A-L-L-A-$(X2)_m$ |
| SEQ ID NO: 60 | $(X1)_n$-K-L-A-V-L-L-A-L-L-A-$(X2)_m$ |

In these sequences, X1 and X2 are selected from one or more charged amino acid residues (e.g. K, R, E, D, etc.), where each X1 and each X2 may be the same or different charged amino acid residue; n has a value of 0 or 3-10, and m has a value of 0 or 3-10, but wherein m and n are not both 0. In one embodiment either m=0 or n=0. As noted above, one example of a solubility tag is R-R-K-K (SEQ ID NO: 17). In a preferred embodiment, all of the charged amino acid residues of the solubility tag are positively charged amino acid residues.

The antiviral peptides of the present invention may also have various reactive tags attached to their terminal amino acid residues. Such tags may be useful in detection and/or removal of the synthetic peptides of the present invention. Such tags may include, by way of example only, biotin, as well as any other tags well-known in the art.

Derivatives of the antiviral peptides of the present invention may also be useful as antiviral peptides. Derivatives of the antiviral peptides include peptides wherein one or more of the amino acid residues are deleted to yield fragments or are substituted for other amino acid residues. For instance, it has been discovered that one or more proline residue may be deleted from the peptides of the present disclosure, without loss of antiviral activity. For example, SEQ ID NO: 32, having the sequence RRKKVALLAVLLALLA is a derivative of SEQ ID NO: 19. Specifically, SEQ ID NO: 32 is the SEQ ID NO: 19 peptide, minus two proline residues. SEQ ID NO: 32 retains antiviral activity, as demonstrated in the examples, even in the absence of the two proline residues. Likewise, SEQ ID NOs: 44 and 45 are derivatives of SEQ ID NOs: 21 and 22, respectively, and SEQ ID NO: 43 is a derivative of the EB peptide. Specifically, SEQ ID NOs: 43, 44, and 45 are the EB peptide and SEQ ID NOs: 21 and 22, respectively, minus two proline residues. SEQ ID NOs: 43-45 retain antiviral activity, as demonstrated in the examples, even in the absence of the two proline residues. These results suggest that proline residues may be dispensable for antiviral activity in the antiviral peptides of the present disclosure. Thus, in one aspect, the present disclosure is directed to antiviral peptides wherein one or more proline residue has been removed from the peptide. Advantageously, removing the proline residue from the antiviral peptides produces shorter (and thus less costly) antiviral peptides, without a subsequent loss of antiviral activity.

Derivatives of the antiviral peptides also include peptides wherein one or more of the amino acid residues are substituted for other amino acid residues. Substitutions may be conservative or may be sequence rearrangements. Conservative substitutions are well known to those of skill in the art; amino acids of similar or identical charge, size or hydrophobicity may be substituted for each other. For example, lysine and arginine are conservative substitutions for each other, as are aspartic and glutamic acids, phenylalanine, tyrosine, and tryptophan, and so forth. Rearranged sequences are those in which one or more amino acids are moved from their original position to a new position within the sequence of the inventive peptide.

Antiviral peptide fragments of the invention can have deletions of 1, 2, 3, 4, 5, 6, 7, 8, 9, 10, 11, 12 or more amino acids, and substituted derivatives can have 1, 2, 3, 4, 5, 6, 7, 8, 9, 10 or more substitutions. In some embodiments, derivatives of the antiviral peptides have both deletions and substitutions.

Substituted peptides or fragments of the peptides must retain antiviral activity to remain within the scope of the disclosure. The antiviral peptides according to the present disclosure or derivatives thereof can be tested for antiviral activity via the methodology described in the following Examples.

The peptides of the present invention can be prepared by processes which incorporate methods commonly used in peptide synthesis such as classical solution coupling of amino acid residues and/or peptide fragments, and, if desired, solid phase techniques. Any method for peptide synthesis well known in the art may be used, for example, Schroeder and Lubke, in "The Peptides", Vol. 1, Academic Press, New York, N.Y., pp. 2-128 (1965); "The Peptides: Analysis, Synthesis, Biology", (E. Gross et al., Eds.), Academic Press, New York, N.Y., Vol. 1-8, (1979-1987); Stewart and Young, in "Solid Phase Peptide Synthesis", 2nd Ed., Pierce Chem. Co., Rockford, Ill. (1984); Wild et al., Proc. Natl. Acad. Sci. USA, 89: 10537 (1992); and Rimsky et al., *J Virol,* 72: 986 (1998); Chan & White in "Fmoc Solid Phase Peptide Synthesis: A Practical Approach", Oxford University Press, (2000).

The present peptides exhibit antiviral activity against respiratory viruses, including various types of influenza, such as influenza A and influenza B. Advantageously, the antiviral peptides of the present disclosure exhibit antiviral activity against numerous strains of influenza, including seasonal, avian (e.g., H5N1 strains), and swine influenzas. Illnesses resulting from infections by these viruses can also be treated according to some of the present methods.

A method for demonstrating the inhibitory effect of the antiviral peptides of the present invention on viral replication is taught in the following Examples. Such methods are also well known in the art. The therapeutic efficacy of the antiviral peptides as antiviral agents can be demonstrated in laboratory animals, for example, by using a murine model. See, e.g., Jones, et al., *J. Virol,* 2006, Vol. 80, No. 24, pp. 11960-11967. Additionally, the therapeutic effect of the pharmacologically active peptides of the present invention can be shown in humans via techniques well-known in the art.

Advantageously, the antiviral peptides of the present disclosure may demonstrate significant antiviral activity against influenza virus. As used herein, the term "significant antiviral activity" means the antiviral peptide inhibits viral hemagglutination by at least about 50%, as compared to mock treated samples of virus. In certain embodiments, the antiviral peptide inhibits viral hemagglutination by at least about 60%, more preferably by at least about 70%, more preferably by at least about 80%, more preferably by at least about 90%, and more preferably by at least about 95%, as compared to mock treated samples of virus.

It has further been discovered that both the EB peptide and the antiviral peptides of the present disclosure inhibit the attachment of influenza virus to host cells, thus preventing viral infection. Surprisingly, it has further been discovered that EB and some of the antiviral peptides of the present disclosure demonstrate antiviral activity through different mechanisms. Without wishing to be bound to any particular theory, it is believed that the EB peptide inhibits attachment of influenza virons to host cells by inducing aggregation of intact influenza virons, thus preventing the virus from infecting the host cell. In contrast, it has been discovered that some of the antiviral peptides of the present disclosure are virucidal. For instance, as is demonstrated in Examples 3 and 4 below, SEQ ID NO: 32 has been shown to have virucidal activity through disruption of lipid membranes.

An antiviral peptide of the present disclosure can be employed as an antiviral agent by administering the peptide topically, intranasally, or through parenteral administration, such as through sub-cutaneous injection, intra-muscular injection, intravenous injection, intraperitoneal injection, or intra-dermal injection, to a warm-blooded animal, e.g., humans, horses, other mammals, etc. The antiviral peptides can be used individually or in combination. Additionally, the antiviral peptide may be administered alone or as part of a composition that further comprises one or more pharmaceutically acceptable carriers, the proportion of which is determined by the solubility and chemical nature of the peptide, chosen route of administration and standard biological administration. Because inventive peptides may target proteins on the surfaces of the virus and/or the cell, to ensure efficacy, the carrier in such formulations should be free or substantially free (e.g., better than 90, 95, 98, or 99 wt %) of proteins that bind to the peptides.

Suitable pharmaceutically acceptable carriers for the compositions containing the peptides are described in the standard pharmaceutical texts. See, e.g., "Remington's Pharmaceutical Sciences", $18^{th}$ Ed., Mack Publishing Company, Easton, Pa. (1990). Specific non-limiting examples of suitable pharmaceutically acceptable carriers include water, saline, dextrose, glycerol, ethanol, or the like and combinations thereof. In addition, if desired, the composition can further contain minor amounts of auxiliary substances such as wetting or emulsifying agents, pH buffering agents that enhance the antiviral effectiveness of the composition.

Depending on the route of administration, the composition may take the form of a solution, suspension, tablet, pill, capsule, sustained release formulation, powder, cream, lotion, emulsion, or the like.

For topical administration, the antiviral peptide can be formulated into a composition containing an effective amount of the antiviral peptide, typically 0.01 or 0.1 to 10%, of the antiviral peptide. Such compositions are typically in the form of a solution, cream, lotion, or emulsion. The antiviral peptides of the present disclosure may be used for treating viral infections of the respiratory tract.

For parenteral administration, the antiviral peptides of the present disclosure may be administered by intravenous, subcutaneous, intramuscular, intraperitoneal, or intradermal injection, alone or in compositions further comprising pharmaceutically accepted carriers. For administration by injection, it is preferred to use the antiviral peptide in a solution in a sterile aqueous vehicle which may also contain other solutes such as buffers or preservatives as well as sufficient quantities of pharmaceutically acceptable salts or of glucose to make the solution isotonic. The antiviral peptides of the present disclosure can be obtained in the form of therapeutically acceptable salts that are well-known in the art.

Because the antiviral peptides of the present disclosure have shown activity against respiratory viruses, the antiviral peptides can also be delivered locally to the respiratory system, for example to the nose, sinus cavities, sinus membranes or lungs. The peptide(s), or pharmaceutical compositions containing one or more peptides, can be delivered to the respiratory system in any suitable manner, such as by inhalation via the mouth or intranasally. The present compositions can be dispensed as a powdered or liquid nasal spray, suspension, nose drops, a gel or ointment, through a tube or catheter, by syringe, by packtail, by pledget, or by submucosal infusion. The peptides may be conveniently delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the peptide and a suitable powder base such as lactose or starch. Examples of intranasal formulations and methods of administration can be found in PCT publications WO 01/41782, WO 00/33813, and U.S. Pat. Nos. 6,180,603; 6,313,093; and 5,624,898. The latter-cited U.S. patents are incorporated herein by reference and for all purposes. A propellant for an aerosol formulation may include compressed air, nitrogen, carbon dioxide, or a hydrocarbon based low boiling solvent. The peptide or peptides of the present disclosure can be conveniently delivered in the form of an aerosol spray presentation from a nebulizer or the like. In some aspects, the active ingredients (i.e., peptides) are suitably micronised so as to permit inhalation of substantially all of the active ingredients into the lungs upon administration of the dry powder formulation, thus the active ingredients will have a particle size of less than 100 microns, desirably less than 20 microns, and preferably in the range 1 to 10 microns. In one embodiment, one or more of the antiviral peptides are packaged into a device that can deliver a predetermined, and generally effective, amount of the peptide via inhalation, for example a nasal spray or inhaler.

The optimal concentration of the peptide or peptides will necessarily depend upon the specific peptide(s) used, the characteristics of the patient, and the nature of the viral infection for which the treatment is sought. These factors can be determined by those of skill in the medical and pharmaceutical arts in view of the present disclosure. In general, the antiviral peptides are most desirably administered at a concentration level that will generally afford antiviral effective results against the selected virus(es) without causing any harmful or deleterious side effects. Generally, an effective amount of antiviral peptide is desired. An effective amount refers to that amount of the peptide that results in a degree of amelioration of symptoms relative to the status of such symptoms prior to treatment, or to an amount effective to prevent or decrease the severity of symptoms after administration of the peptide. Specific dosages may be adjusted depending on conditions of disease, the age, body weight, general health conditions, sex, diet of the subject, dose intervals, administration routes, excretion rate, and combinations of drugs. Any of the above dosage forms containing effective amounts are well within the bounds of routine experimentation and therefore, well within the scope of the instant disclosure. A therapeutically effective dose may vary depending upon the route of administration and dosage form.

It will be appreciated by those skilled in the art that reference herein to treatment extends to prophylaxis as well as the treatment of established infections or symptoms.

It will be further appreciated that the amount of an antiviral peptide of the present disclosure that is useful in treatment or prevention of influenza will vary not only with the particular peptide selected but also with the route of administration, the nature of the condition being treated, and the age and condition of the patient, and will ultimately be at the discretion of the attendant physician or veterinarian. In general however, a suitable dose will be in the range of from about 0.01 to 750 mg/kg of body weight per day preferably in the range of 0.1 to 100 mg/kg/day, most preferably in the range of 0.5 to 25 mg/kg/day.

The peptides of the present disclosure may be administered therapeutically or prophylactically. Treatment is preferably commenced before or at the time of infection or at the time the mammal is exposed to a virus that is capable of causing a viral respiratory infection, and continued until virus is no longer present or active in the respiratory tract. However, the treatment can also be commenced post-infection, after the mammal has been exposed to a virus that is capable of causing a viral respiratory infection, or after the appearance of established symptoms of infection.

Suitable treatment is given 1-4 times daily and continued for 3-10 days, and typically 8 days post infection.

The desired dose may be presented in a single dose or as divided doses administered at appropriate intervals, for example as two, three, four or more sub-doses per day.

The peptide may be conveniently administered in unit dosage form, for example, containing 10 to 1500 mg, conveniently 20 to 1000 mg, most conveniently 50 to 700 mg of active ingredient per unit dosage form, e.g. 1 mg/kg equates to 75 mg/75 kg of body weight.

The present peptides can also be provided as pharmaceutically acceptable salts. A "pharmaceutically acceptable salt" includes a salt with an inorganic base, organic base, inorganic acid, organic acid, basic amino acid, or acidic amino acid. As salts of inorganic bases, the disclosure includes, for example, alkali metals such as sodium or potassium; alkaline earth metals such as calcium and magnesium or aluminum; and ammonia. As salts of organic bases, the disclosure includes, for example, trimethylamine, triethylamine, pyridine, picoline, ethanolamine, diethanolamine, and triethanolamine. As salts of inorganic acids, the instant disclosure includes, for example, hydrochloric acid, hydroboric acid, nitric acid, sulfuric acid, and phosphoric acid. As salts of organic acids, the instant disclosure includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant disclosure includes, for example, arginine, lysine and ornithine. Acidic amino acids include, for example, aspartic acid and glutamic acid.

The present disclosure is further described with reference to the following illustrated Examples. Unless defined otherwise, all technical and scientific terms used herein have the same meaning as commonly illustrated by one of ordinary skill in the art of the invention. Although any methods and materials similar or equivalent to those described herein can be used in the practice of the invention, the preferred methods and materials have been described. Unless mentioned otherwise, the techniques employed or contemplated herein are standard methodologies well-known to one of ordinary skill in the art. The materials, methods and Examples are illustrative only and not limiting. All references cited herein are incorporated by reference.

Having described the disclosure in detail, it will be apparent that modifications and variations are possible without departing from the scope of the disclosure defined in the appended claims.

EXAMPLES

The following non-limiting examples are provided to further illustrate the present disclosure.

Test Methods

Cell culture and virus: A/PuertoRico/8/34 (PR/8, H1N1) and A/Turkey/Wisconsin/68 (Tk/Wi H5N1) were propagated in 10 day-of-age specific pathogen-free embryonated chicken eggs (Sunnyside Farms, Beaver Dam, Wis.) at 37° C. for 48 hours. The allantoic fluid was harvested, centrifuged for clarification, and virus purified by overlyaing on a 30-60% discontinuous sucrose gradient. The virus layer was extracted from the 30-60% interface using a SW28 rotor centrifuge at 26,000 rpm for 90 minutes, and pelleted by another round of ultracentrifugation at 26,000 rpm for 60 minutes. PR/8 was also propagated in Madin-Darby canine kidney (MDCK, ATCC, Manassas, Va.) cells and culture superantants harvested 48 to 72 hours post infection (hpi), centrifuged for clarification, and stored at −70° C. Viral titers were determined by fifty percent tissue culture infectious dose ($TCID_{50}$) analysis in MDCK cells, and evaluated as described in Reed and Muench, *Am. J. Hyg*., Vol. 27, pp. 493-497 (1938). MDCK cells were cultured in modified Eagle's medium (MEM, CellGro, Herndon, Va.) supplemented with 4.5 grams of glucose per liter, 2 mM glutamine, and 10% fetal bovine serum (FBS, Gemini Bio-Products, West Sacramento, Calif.) at 37° C., 5.5% $CO_2$. Recombinant hemagglutinin (HA) from A/Vietnam/1203/04 (H5N1) was purchased from Protein Sciences (Meriden, Conn.).

Purification of viral hemagglutinin: Viron-associated hemagglutinin (HA) was purified from Tk/Wi and PR/8 influenza virus particles as described in Johansson, et al., Journal of Virology, 1989, Vol. 63(3), p. 1239-1246, with several modifications. Briefly, virus was collected from the allantoic fluid of infected hen's eggs and sucrose purified as described above. Pellets were resuspended in 0.5 mL of sodium acetate buffer (0.05 M sodium acetate, 2 mM $CaCl_2$, 0.2 mM EDTA, pH to 7.0), homogenized through an 18-gauge needle, and mixed with an equal volume of 15% octylglucoside (octyl-β-d-thioglucoside; Fisher Scientific, Norcross, Ga.) in sodium acetate buffer, followed by vigorous vortexing for 5 minutes. This suspension was centrifuged at 18,400×g for 60 minutes at 4° C., and the supernatant carefully removed and reserved as the HA-rich fraction. Two percent aqueous cetyltrimethylammonium bromide (CTAB, Bio-World, Dublin, Ohio) was added to the HA fraction to a final concentration of 0.1% CTAB, and the sample was applied to a DEAE-Sephadex (A-50; GE Healthcare, Uppsala, Sweden) ion-exchange column (bed, 0.7 cm×6.0 cm) previously swollen and equilibrated with 0.05 M Tris-hydrochloride (pH 7.5) containing 0.1% octylglucoside. Twenty 0.5 mL fractions were collected by gravity with low salt HA elution buffer (0.05 M TrisHCl, 0.1 M NaCl, 0.1% Triton X-100, pH to 7.5) and again with a high salt HA elution buffer (0.05 M TrisHCl, 0.2 M NaCl, 0.1% Triton X-100, pH to 7.5). Individual fractions were assayed for HA activity and analyzed for purity by SDS-polyacrylamide gel electrophoresis under non-reducing conditions followed by staining with colloidal commassie. Protein concentration was determined by BCA assay as per manufacturer's instructions (Pierce, Rockford, Ill.). For experiments requiring concentrated HA, fractions were centrifuged under vacuum for 1.5 hours at 30° C., pooled and dialyzed against phosphate buffered saline (PBS) containing 0.01% Tween-20 (PBST) for 12 hours at 4° C. The concentrated HA was again tested for activity and protein concentration.

Peptide synthesis: Synthesis and analysis of peptides was performed by EZBiolab, Inc. (Westfield, Ind.) using a solid state method. Initially, a library of non-HPLC purified truncations of the EB peptide was synthesized using a 96-well plate format. The synthesized peptides (including EB) are listed in Table 3. Any peptides with antiviral activity, and several negative controls, were synthesized on a larger scale, and purified by HPLC with purity that met or exceeded 90%. The peptides chosen for extensive study include EB, a sequence scrambled control (EBX), as well as a 16 amino acid peptide that is a truncation of EB, with both proline residues deleted (SEQ ID NO: 32).

Plaque reduction assay: MDCK cells ($5.5\times10^5$ cells per well) in a 6-well tissue culture dish were washed with PBS and incubated with PR/8 virus (MOI 0.005) pre-treated with 0 μM to 30 μM concentrations of peptide for 1 hour at 37° C. After a one hour incubation, monolayers were washed and overlaid with 1.6% SeaKem LE agarose (Cambrex, Rockland Me.) diluted 1:1 with media containing 2× L-15 (Lonza, Walkerville, Md.), 40 mM Hepes, 0.15% sodium bicarbonate, 2 mM L-glutamine, 1× penicillin/streptomycin, and incubated for 72 hours at 37° C. Overlays were then carefully removed, fixed with 10% formalin, and stained with crystal violet.

Sedimentation density profiles: PR/8 virus (512 HA units) was treated with 0 (mock), 10, or 30 μM concentrations of peptide for 1 hour at 37° C. and layered on a continuous 20-60% sucrose gradient. Samples were subjected to ultracentrifugation in a Beckman SW-41 at 18,000 rpm for 90 minutes. Samples (500 μL) were collected from the bottom of the tube and 7 μL of each fraction was dotted to nitrocellulose, blocked with 3% milk in Tris-buffered saline containing 0.1% Tween-20 (TTBS) and probed with goat anti-hemagglutinin serum (1:1000 in TTBS) for 1 hour at room temperature, followed by donkey anti-goat IgG (1:2000, Santa Cruz Biotechnology, Santa Cruz, Calif.). Immune complexes were detected by enhanced chemiluminescence (Pierce, Rockford, Ill.). The density of each sucrose fraction was determined by measuring refractive index in a Bausch and Lomb 334610 Refractometer (Rochester, N.Y.).

Electron microscopy: Purifed PR/8 virus (512 HA units) was treated with PBS alone (mock) or 10 μM of the different peptides for 1 hour at 37° C. Samples (10 μl) were adsorbed to poly-L-lysine coated grids for 5 min at 23° C. The grids were rinsed with PBS, stained with 2% phosphotungstic acid (PTA) in water adjusted to pH 6, and air dried. Alternatively, virus was preadsorbed to grids and treated with peptides thereafter. A total of $4\times10^9$ PFU of purified PR/8 per ml in 5 μl of PBS was applied to the coated grids for 5 min at 23° C., and the grids were rinsed once with serum-free DMEM buffered with 25 mM HEPES (pH 7.4) and treated with 15 μl of 5 mM of the peptide being tested in the same medium for 30 min at 37° C. The pH of highly concentrated solutions of peptide was readjusted to 7.4 with NaOH prior to use. To prevent evaporation of the peptide-containing solutions, each grid was held in a Hiraoka flexible staining plate and covered with a miniature bell jar made from a 0.5-ml polypropylene microcentrifuge tube, small enough for the 15 μl to fill half of the bell jar facing the coated surface of the grid. The entire assembly was then incubated in a moist chamber for 30 min at 37° C. After treatment, grids were rinsed twice with DMEM and once with PBS before they were stained with PTA and dried. Grids were examined in a JEOL JEM-1200EX electron microscope at magnifications of ×15,000 and ×40,000.

Hemagglutination (HA) assay: Hemagglutination of chicken red blood cells (cRBCs, Lampire Biological Laboratories, Pipersville, Pa.) was carried out in round bottom 96-well microtiter plates by preparing two-fold dilutions of viral samples in PBS, as described in Jones, et al., *Journal of Virology,* 80(24):11960-11967 (2006). Titer was reported as hemagglutinating units per 50 μL (HAU/50 μL) of sample.

Hemoglobin Release Assay: The ability of peptides to compromise red blood cell (RBC) lipid membranes was assessed by measuring release of hemoglobin as described in Cianci, et al., *Journal of Virology,* 73(3):1785-94 (1999), with slight modifications. Briefly, 100 μL aliquots of 0.5% cRBC solution were treated with 0 μM to 30 μM concentrations of peptides for 1 hour at 37° C. Samples were spun at 600×g for 3 minutes and the supernatants removed to clear, flat bottom 96-well plates. Absorbance at a wavelength of 540 nm was measured on a SpectraMax 250 spectrophotometer (Molecular Devices, Sunnyvale, Calif.).

Trypsin protection assay: Purified viron HA in the presence or absence of peptides was assayed for conformation-induced trypsin sensitivity, as described in Cianci, et al., *Journal of Virology,* 73(3):1785-94 (1999). Briefly, purified HA (10 μg) was treated with 0 (mock), 10, or 30 μM peptide for 1 hour at 37° C., or acidified with 0.25 M sodium citrate (pH 4.2) for 15 minutes at 37° C., followed by neutralization with 0.25 Tris-HCl (pH 9.0) as a positive control. TPCK-trypsin (5 μg, Sigma Immunochemicals, St. Louis, Mo.) was added to all samples, and the samples were incubated for 1 hour at 37° C. and resolved by SDS-PAGE. Gels were stained with Proteo-Blue colloidal coomassie (National Diagnostics, Atlanta, Ga.), and the digestion of the $HA_1$ (56 kD) subunit of HA was used as positive evidence of the conformational shift.

EB Inhibition Assay: A/Vietnam/1203/2004 H5N1 influenza virus (VN/1203) HA peptides were obtained through the NIH Biodefense and Emerging Infections Research Resources Repository (NR-2704, NIAID, NIH). Briefly, 0, 3, 7.5 or 15 μM HA peptide was incubated in the presence or absence of 2.5 μM EB at 37° C. After 1 hour, PR/8 virus (64 HAU) or PBS was added to each reaction and reactions were incubated at 37° C. for 1 hour. Hemagglutination activity of PR/8 virus was performed as described above. Hemagglutination activity was not detected for the VN/1203 peptides alone.

Statistical Analysis: All data were performed in triplicate and are representative of at least 3 separate experiments. The results represent the means±standard deviations of triplicate determinations. Statistical significance of the data was determined by using analysis of variance (ANOVA) or Student's t-test.

Example 1

In this example, derivatives of the EB peptide were screened for anti-influenza virus activity.

Individual amino acids were deleted from the N- or C-termini of the consensus EB peptide (SEQ ID NO: 1) to form a series of truncated EB peptides, as described above. For each peptide, the N-terminal RRKK (SEQ ID NO: 17) tetrapeptide for solubility was maintained. The EB peptide was also synthesized without the proline residues. The resulting peptide had the following sequence: RRKKAAVALLAVLLALLA (SEQ ID NO: 43). Also synthesized was a 20-amino acid control peptide EBX, in which the amino acids making up the EB peptide sequence were scrambled. EBX had the following sequence: RRKKLAALPLVLAAPLAVLA (SEQ ID NO: 31). The EBX peptide was also synthesized without two of the proline residues and a leucine residue (SEQ ID NO: 30). Also synthesized was the truncated peptide having SEQ ID NO: 19 without the proline residues. The resulting peptide had the following sequence: RRKKVALLAVLLALLA (SEQ ID NO: 32). The truncated peptide having SEQ ID NO: 21 was also synthesized without the proline residues. The resulting peptide had the following sequence: RRKKLLAVLLALLA (SEQ ID NO: 44). The truncated peptide having SEQ ID NO: 22 was also synthesized without the proline residues. The resulting peptide had the following sequence: RRKKLAVLLALLA (SEQ ID NO: 45). The sequence of each peptide evaluated is shown in Table 3.

Each peptide was screened for the ability to inhibit viral hemagglutination. Purified PR/8 virus (64 HAU/50 μL), prepared as described above, was treated with PBS alone (mock) or 10 μM of each peptide listed in Table 3 for 1 hour at 37° C. and doubling dilutions incubated with cRBCs for 1 hour at room temperature. The reciprocal dilution of the last well that agglutinated was determined to be the HA titer, and this value was compared back to the mock treated samples (100% hemagglutination). The results are shown in Table 3.

The 50% effective concentration ($EC_{50}$) of the active peptides was also determined by HA inhibition assay using peptide concentrations of 0.1 μM, 0.5 μM, 1.0 μM, 5.0 μM, and 10 μM, using the method described above. The results are shown in Table 3.

TABLE 3

| Peptide | C- or -N terminus deletion | Sequence | HA inhibition[a] | %[b] inhibition | $EC_{50}$[c] (μM) |
|---|---|---|---|---|---|
| EB (SEQ. ID. NO: 1) | n/a | RRKKAAVALLPAVLLALLAP | Yes | 95 ± 2% | 2.6 ± 1.0 |
| SEQ. ID. NO: 2 | -1C | RRKKAAVALLPAVLLALLA | Yes | 94 ± 2% | 0.5 ± 0.3 |
| SEQ. ID. NO: 3 | -2C | RRKKAAVALLPAVLLALL | Yes | 95 ± 2% | 0.6 ± 0.3 |
| SEQ. ID. NO: 4 | -3C | RRKKAAVALLPAVLLAL | Yes | 89 ± 3% | 3.8 ± 1.9 |
| SEQ. ID. NO: 5 | -4C | RRKKAAVALLPAVLLA | Yes | 96 ± 3% | 2.8 ± 1.1 |
| SEQ. ID. NO: 6 | -5C | RRKKAAVALLPAVLL | No | 0% | |
| SEQ. ID. NO: 7 | -6C | RRKKAAVALLPAVL | No | 0% | |
| SEQ. ID. NO: 8 | -7C | RRKKAAVALLPAV | No | 0% | |
| SEQ. ID. NO: 9 | -8C | RRKKAAVALLPA | No | 0% | |
| SEQ. ID. NO: 10 | -9C | RRKKAAVALLP | No | 4 ± 8% | |
| SEQ. ID. NO: 11 | -10C | RRKKAAVALL | No | 0% | |
| SEQ. ID. NO: 12 | -11C | RRKKAAVAL | No | 0% | |
| SEQ. ID. NO: 13 | -12C | RRKKAAVA | No | 0% | |
| SEQ. ID. NO: 14 | -13C | RRKKAAV | No | 0% | |
| SEQ. ID. NO: 15 | -14C | RRKKAA | No | 0% | |
| SEQ. ID. NO: 16 | -15C | RRKKA | No | 0% | |
| SEQ. ID. NO: 17 | -16C | RRKK | No | 0% | |
| SEQ. ID. NO: 18 | -1N | RRKKAVALLPAVLLALLAP | Yes | 94 ± 6% | 0.8 ± 0.3 |
| SEQ. ID. NO: 19 | -2N | RRKKVALLPAVLLALLAP | Yes | 94 ± 4% | 0.5 ± 0.4 |
| SEQ. ID. NO: 20 | -3N | RRKKALLPAVLLALLAP | Yes | 94 ± 3% | 0.7 ± 0.3 |

TABLE 3-continued

| Peptide | C- or -N terminus deletion | Sequence | HA inhibition[a] | %[b] inhibition | $EC_{50}$[c] (μM) |
|---|---|---|---|---|---|
| SEQ. ID. NO: 21 | -4N | RRKKLLPAVLLALLAP | Yes | 94 ± 4% | 0.8 ± 0.3 |
| SEQ. ID. NO: 22 | -5N | RRKKLPAVLLALLAP | Yes | 94 ± 4% | 0.9 ± 0.3 |
| SEQ. ID. NO: 23 | -8N | RRKKVLLALLAP | Yes | 90 ± 4% | 4.0 ± 0.8 |
| SEQ. ID. NO: 24 | -9N | RRKKLLALLAP | No | 0% | |
| SEQ. ID. NO: 25 | -11 | RRKKALLAP | No | 0% | |
| SEQ. ID. NO: 26 | -12N | RRKKLLAP | No | 0% | |
| SEQ. ID. NO: 27 | -13N | RRKKLAP | No | 0% | |
| SEQ. ID. NO: 28 | -14N | RRKKAP | No | 0% | |
| SEQ. ID. NO: 29 | -15N | RRKKP | No | 0% | |
| SEQ. ID. NO: 30 | EBX, -1 leucine, no prolines | RRKKAALLVLAALAVLA | No | 0% | |
| SEQ. ID. NO: 31 | EBX | RRKKLAALPLVLAAPLAVLA | No | 0% | |
| SEQ. ID. NO: 32 | -2N, no prolines | RRKKVALLAVLLALLA | Yes | 94 ± 4% | 0.5± 0.5 |
| SEQ. ID. NO: 43 | EB, no prolines | RRKKAAVALLAVLLALLA | Yes | 95 ± 2% | 1.6± 1.2 |
| SEQ ID NO: 44 | -4N, no prolines | RRKKLLAVLLALLA | Yes | 95 ± 2% | 3 |
| SEQ. ID. NO: 45 | -5N, no prolines | RRKKLAVLLALLA | Yes | 94 ± 0% | 3 |

[a]10 μM of each peptide was screened for the ability to inhibit hemagglutination of 64 HA units of purified A/PR/8/34. Results are indicative of 2-4 independent screens.
[b]Hemagglutinating units of a mock treated sample of virus (64 HAU) were reported as 100% and all values were normalized to this and expressed as percent inhibition. Results are indicative of 2-4 independent screens.
[c]0.1-10 μM of each peptide was assayed for the ability to inhibit hemagglutination of 64 HA units of purified PR/8. $EC_{50}$ values were estimated from the dose response curves. Results are indicative of at least 4 independent tests.

As can be seen from Table 3, a maximum of 4 amino acids from the C-terminus could be deleted from the EB peptide without loss of anti-viral activity. In contrast, up to 8 amino acids could be deleted from the N-terminus, excluding the RRKK (SEQ ID NO: 17) solubility tag, of the EB peptide without significant loss of anti-viral activity. In total, 14 active EB truncation peptides were identified, i.e., SEQ ID NOs: 2-5, 18-23, 32, and 43-45. The active EB truncation peptides contained 12 to 19 amino acids and maintained significant inhibition (i.e., 89% or greater as compared to mock treated) of HA activity. Additionally, the proline residues at positions 11 and 20 of the EB peptide were dispensable for antiviral activity, as can be seen from Examples 2-5 below, and SEQ ID NO: 43 (95±2% inhibition). The two proline residues from SEQ ID NOs: 21 and 22 were likewise dispensible for anti-viral activity, as both SEQ ID NOs: 44 and 45 exhibited significant inhibition (95±2% inhibition and 94±0% inhibition, respectively). The RRKK (SEQ ID NO: 17) tetrapeptide had no antiviral activity.

Figure 6:
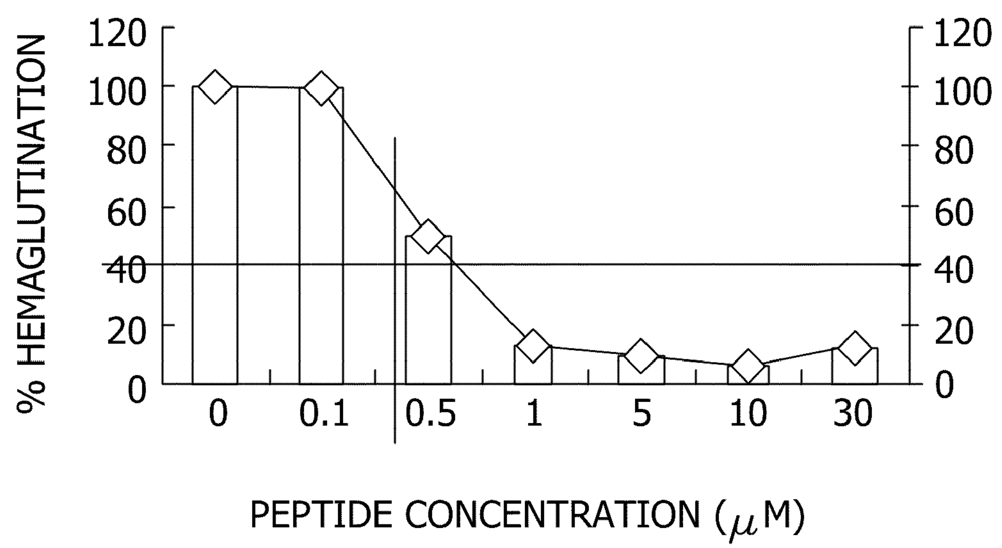
FIG. 6 is a chart depicting the percent (%) hemagglutination for varying concentrations of SEQ. ID NO: 32, as described in Example 1.

Full-length EB peptide had an $EC_{50}$ value of 2.6 μM. Truncated peptide SEQ ID NO: 4, having 3 amino acids deleted from the C-terminal end of EB, SEQ ID NO: 5, having 4 amino acids deleted from the C-terminal end of EB, and SEQ ID NO: 23, having 8 amino acids deleted from the N-terminal end of EB, had slightly higher $EC_{50}$ values as compared to full-length EB. Surprisingly, removal of the C-terminal proline (SEQ ID NO: 2) or proline and alanine (SEQ ID NO: 3) or any of the first 5 amino acids after the RRKK solubility motif at the N-terminal end of EB (SEQ ID NOs: 18-22) led to significantly lower $EC_{50}$ values (0.5-0.9 μM, p<). Additionally, removal of both proline residues from SEQ ID NO: 19 did not result in loss of antiviral activity, as can be seen from Table 3 (SEQ ID NO: 32) and FIG. 6.

Example 2

In this example, the anti-viral activity of the truncated EB peptide having SEQ ID NO. 32 was further characterized.

To begin, the truncated peptide having SEQ ID NO. 32 (RRKKVALLAVLLALLA) was synthesized, as described above. The full length EB peptide (SEQ ID NO: 1), EBX (SEQ ID NO: 31), and SEQ ID NO: 32 were tested for toxicity and anti-viral activity.

The cytotoxic effects of EB and the truncated peptide SEQ ID NO: 32 are shown in FIG. 1A. MDCK cells were mock treated (0 μM peptide) or treated with increasing concentrations (i.e., 5 μM, 10 μM, 20 μM, 30 μM, 50 μM, and 75 μM) of EB or SEQ ID NO: 32 peptides, and cell death determined at 24 hours post infection by a cytotoxicity assay (CellTiter 96®$AQ_{ueous}$ One Solution Cell Proliferation Assay, available from Promega, Catalog No. G3580). Samples were compared and normalized to mock treated cells. As can be seen from FIG. 1A, the full length EB peptide (SEQ ID NO: 1) displayed limited toxicity against MDCK cells. In contrast, SEQ ID NO: 32 displayed significant toxicity with cellular viability decreasing to 20% with 75 μM peptide.

Figure 1B:
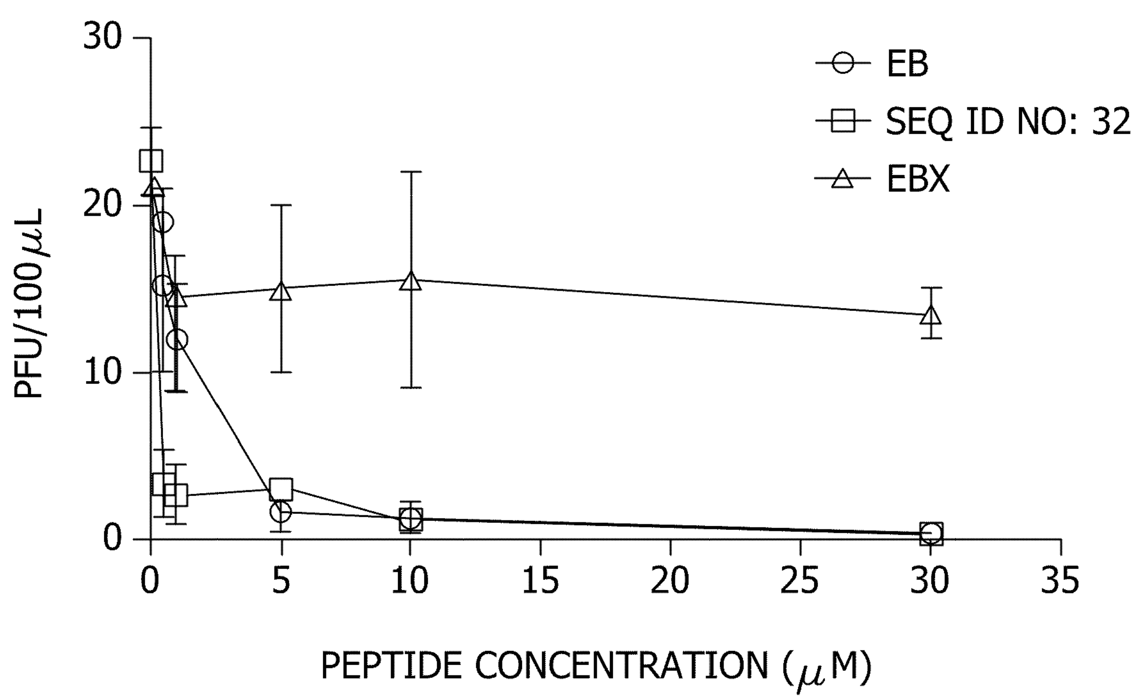
FIG. 1B is a graph depicting the number of plaque forming units per 100 μL of inoculum after treatment of MDCK cells with PR/8 virus that was treated with 0 μM to 30 μM concentrations of EB, EBX, or SEQ ID NO: 32, as described in Example 2. EB is o, SEQ ID NO: 32 is (□), and EBX is Δ. 0 μM results represents the well infected with untreated PR/8. Results are representative of 3 independent experiments.

To measure anti-viral activity, PR/8 virus (MOI 0.005) was treated with either 0 μM, 0.5 μM, 1.0 μM, 5.0 μM, 10.0 μM, or 30 μM concentrations of either EB, EBX (SEQ ID NO: 31), or SEQ ID NO: 32, and plaque assays were performed on MDCK cells, as described above. A control assay was also performed on MDCK cells which were not treated with any virus (mock). Plaques were enumerated from crystal violet stained monolayers 3 days post-infection. The results are shown in FIG. 1B.

PR/8 virus infected cells had approximately 218 plaque forming units (pfu) per mL. Treatment with the scrambled control peptide EBX had no effect on either plaque morphology or numbers. In contrast, full-length EB peptide (SEQ ID NO: 1) inhibited plaque formation in a dose-dependent manner, with approximately 92% plaque reduction at 5 μM or greater concentrations. The truncated peptide having SEQ ID NO: 32 was clearly more active than full-length EB, and reduced virus yield to approximately 85% of virus alone at 0.5 μM and approximately 90% by 1 μM. Mock-infected cells were intact and displayed no plaques. These data demonstrated that the truncated peptide having SEQ ID NO: 32 inhibits influenza virus replication in cells more effectively than the full-length EB peptide.

Example 3

In this example, the ability of the EB peptide to inhibit the attachment of influenza virus to host cells through EB-mediated aggregation of the influenza virion was evaluated.

Density gradient ultracentrifugation was used to isolate potential peptide-induced viral aggregates. PR/8 virus was treated with 0 μM, 10 μM, or 30 μM of either EB (SEQ ID NO: 1), the truncated peptide having SEQ ID NO: 32, or the scrambled EBX peptide (SEQ ID NO: 31) for 1 hour at 37° C., and layered onto a continuous 20-60% sucrose gradient, as described above. After centrifugation at 18,000 rpm for 90 minutes, 0.5 mL fractions were collected, spotted onto nitrocellulose, and probed for HA by immunoblotting and densitometery performed to quantitate HA levels. Further, the HA activity of each fraction was determined. The results are shown in FIG. 2. For FIGS. 2B-2F, the presence of HA antigen in each fraction as determined by immunoblotting is represented by (○) on the first Y axis, and HA activity in each fraction is represented by (□) on the second Y axis. The results are representative of three independent experiments.

Figure 2A:
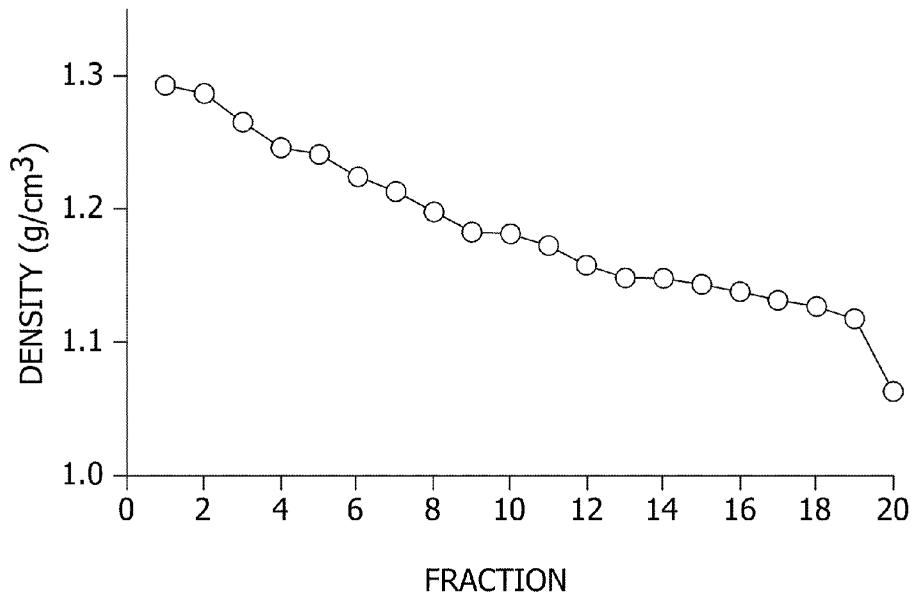
FIG. 2A is a graph depicting the density of gradients obtained through density gradient ultracentrifugation, as described in Example 3.
Figure 2B:
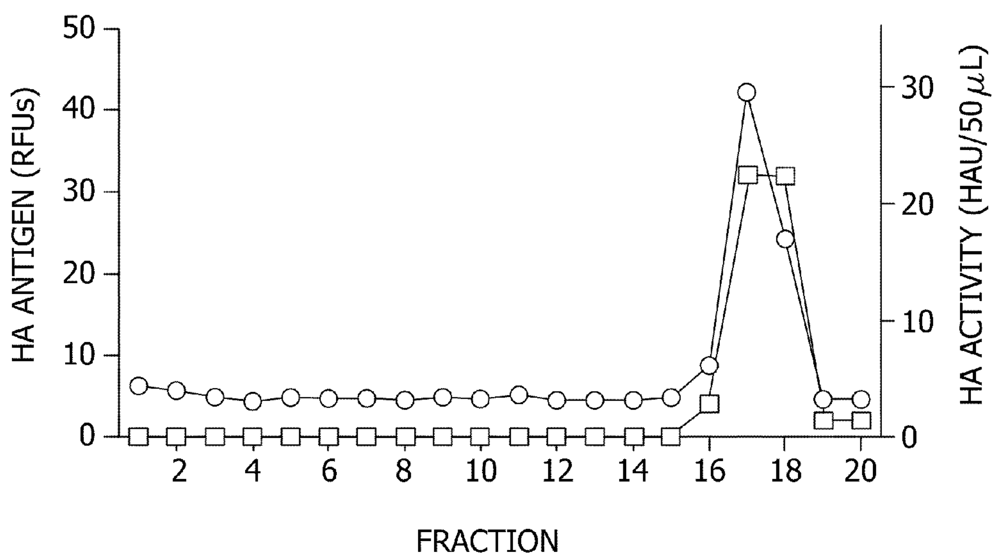
FIG. 2B is a graph depicting the results of density gradient ultracentrifugation for samples of virus treated with PBS (0 μM peptide), as described in Example 3. The presence of HA antigen as determined by immunoblotting is depicted by (○) and hemagglutinating activity is depicted by (□).
Figure 2C:
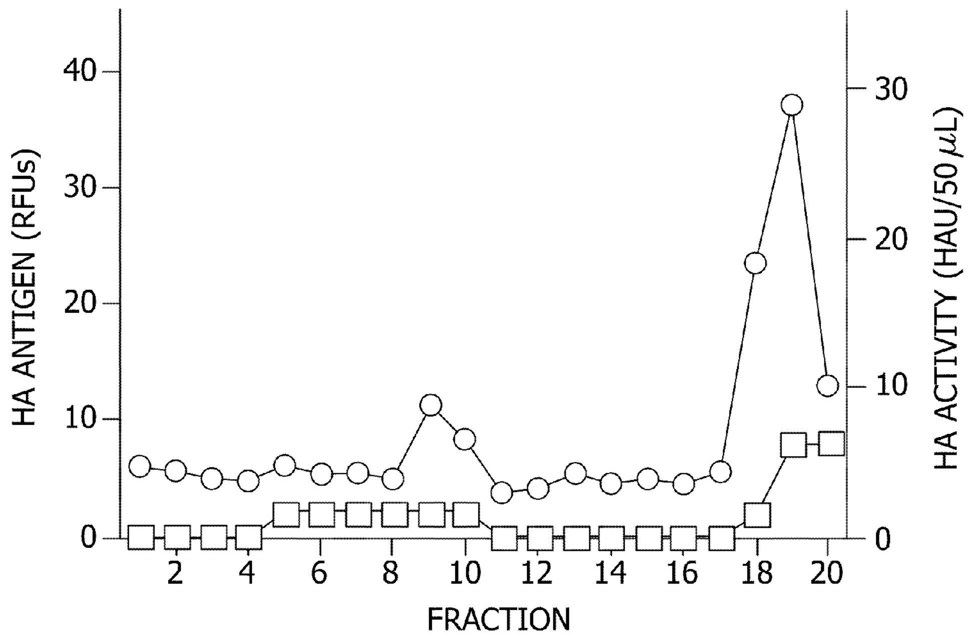
FIG. 2C is a graph depicting the results of density gradient ultracentrifugation for samples of virus treated with 10 μM of EB peptide, as described in Example 3. The presence of HA antigen as determined by immunoblotting is depicted by (○) and hemagglutinating activity is depicted by (□).
Figure 2D:
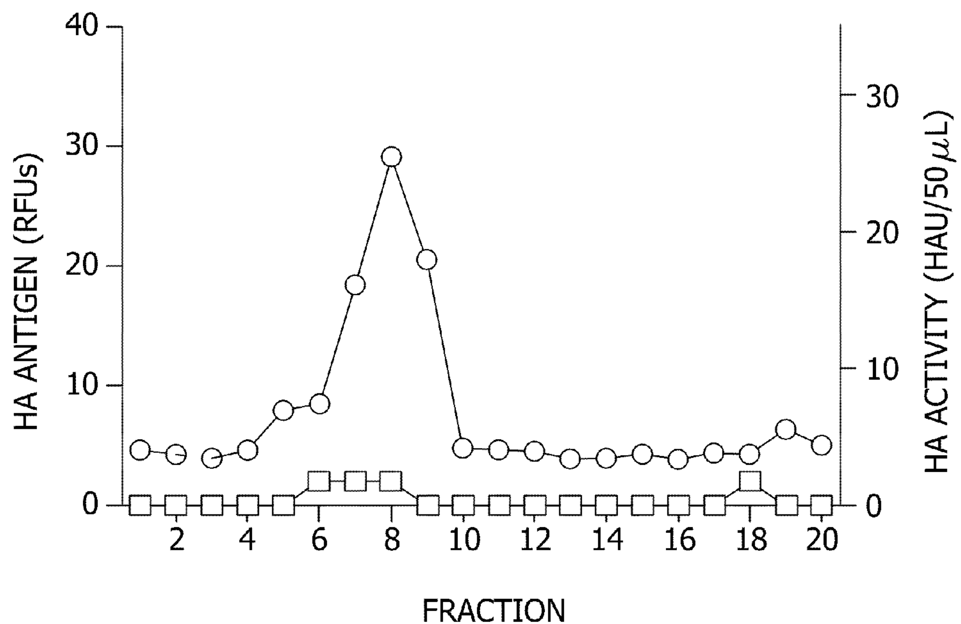
FIG. 2D is a graph depicting the results of density gradient ultracentrifugation for samples of virus treated with 30 μM of EB peptide, as described in Example 3. The presence of HA antigen as determined by immunoblotting is depicted by (○) and hemagglutinating activity is depicted by (□).
Figure 2E:
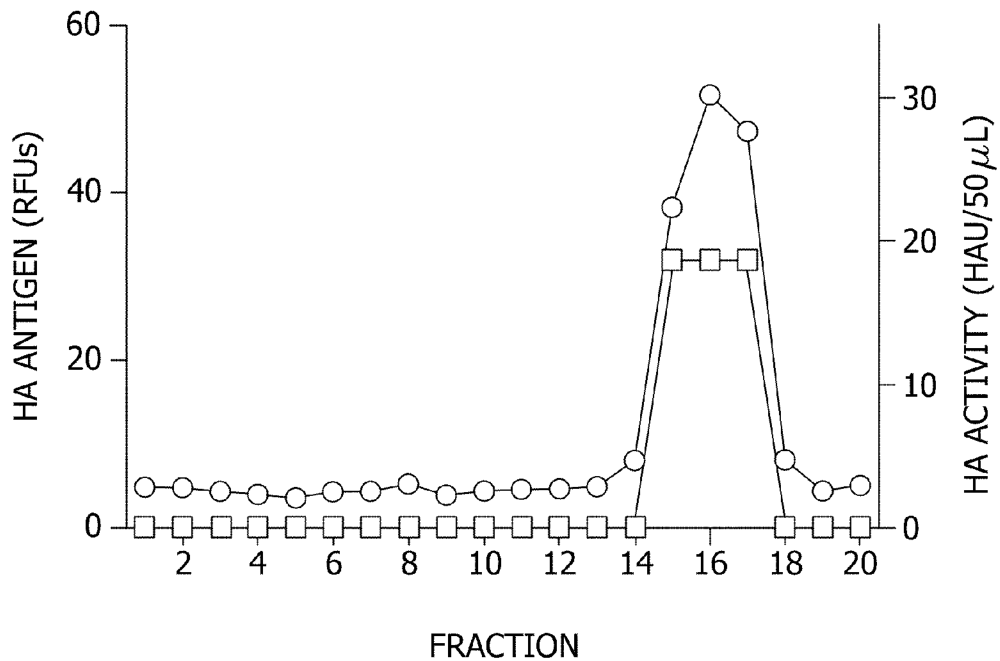
FIG. 2E is a graph depicting the results of density gradient ultracentrifugation for samples of virus treated with 10 μM of EBX, as described in Example 3. The presence of HA antigen as determined by immunoblotting is depicted by (○) and hemagglutinating activity is depicted by (□).
Figure 2F:
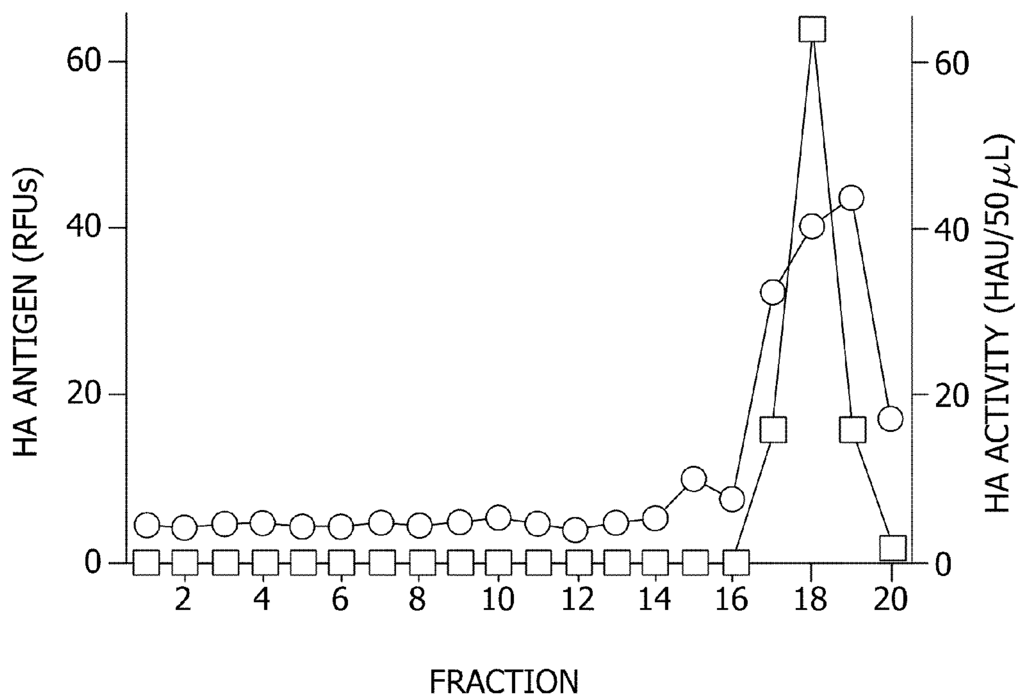
FIG. 2F is a graph depicting the results of density gradient ultracentrifugation for samples of virus treated with 30 μM of EBX, as described in Example 3. The presence of HA antigen as determined by immunoblotting is depicted by (○) and hemagglutinating activity is depicted by (□).

FIG. 2A illustrates the density of the respective gradients. PR/8 virus alone was present in the fractions containing approximately 30% sucrose with a density of 1.14 g/cm$^3$. These fractions also contained HA activity, demonstrating that the purified virus was active, as can be seen from FIG. 2B, which shows results for virus treated with PBS (0 μM peptide). Similar results were found when PR/8 virus was pretreated with the EBX peptide at either 10 μM or 30 μM (see FIG. 2E for 10 μM treatment, and FIG. 2F for 30 μM EBX treatment). In contrast, pretreatment with 10 μM EB peptide resulted in a shift in the location of the HA antigen to the 20% to 45% sucrose fractions, as can be seen from FIG. 2C. Pre-treatment with 30 μM EB peptide (see FIG. 2D) caused an even more dramatic shift with HA antigen localized to the 41-53% sucrose with the majority of virus antigen detected at a density of 1.20 g/cm$^3$. More importantly, HA activity was considerably lower in the EB peptide-treated samples as compared to virus alone, indicating that the aggregates were impaired in their ability to attach to cRBCs. Additionally, the sedimentation profile of virus treated with the peptide having SEQ ID NO: 32 was similar to virus alone (data not shown), yet the fractions containing HA had no detectable HA activity, suggesting a different mechanism of antiviral activity.

To confirm that the peptides induced viral aggregation, purified PR/8 virus (512 HA units) was treated with PBS (mock) or 10 μM of either EB, EBX, or SEQ ID NO: 32 for 1 hour at 37° C., and analyzed by electron microscopy, as described above. The results are shown in FIG. 3.

Figure 3A:
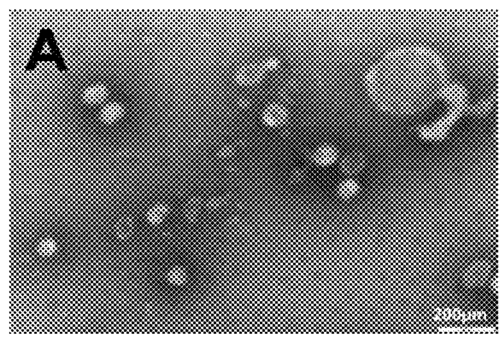
FIG. 3 is a picture from an electron microscope of PR/8 virons that were mock treated (PBS-0 μM peptide) (FIG. 3A) (66,000× magnification) or treated with 10 μM EB peptide (FIG. 3B) (14,000× magnification), 10 μM of SEQ ID NO: 32 (FIG. 3C) (66,000× magnification) or 10 μM of EBX peptide (FIG. 3D) (14,000× magnification), as described in Example 3.
Figure 3B:
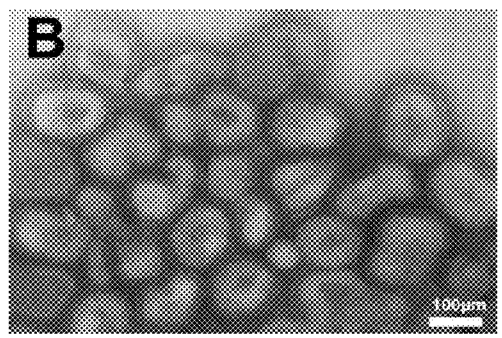
Figure 3C:
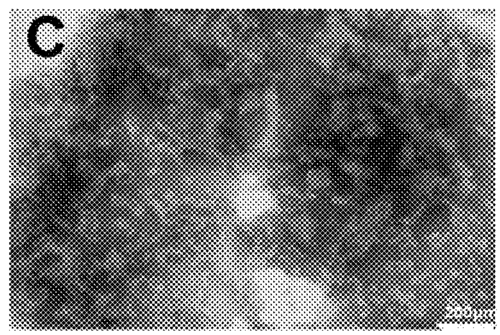
Figure 3D:
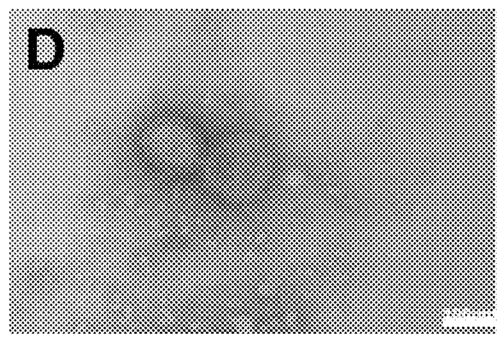

In mock-treated (FIG. 3A) and control EBX peptide-treated samples (FIG. 3D), individual virions were uniformly scattered across the field, with sporadic aggregates (approximately 2 to 4 virions) noted. In contrast, nearly all of the virions treated with full length EB peptide were found in large clusters of 25 to 100 individual viral particles, confirming that EB peptide aggregates influenza virus (FIG. 3B). Surprisingly, PR/8 virus treated with SEQ ID NO: 32 was also found in large aggregates with few individual virions observable in any field, as can be seen in FIG. 3C. However, in contrast to the EB peptide-treated virus, SEQ ID NO: 32 treated virions showed severe alteration to structural integrity, with disruption of membranes and few viral particles intact within the aggregates. Without wishing to be bound to any theory, it is believed that the SEQ ID NO: 32 peptide vas virucidal by disrupting lipid membranes.

Example 4

In this example, the virucidal activity of the SEQ ID NO: 32 peptide through disruption of lipid membranes was confirmed.

Figure 4:
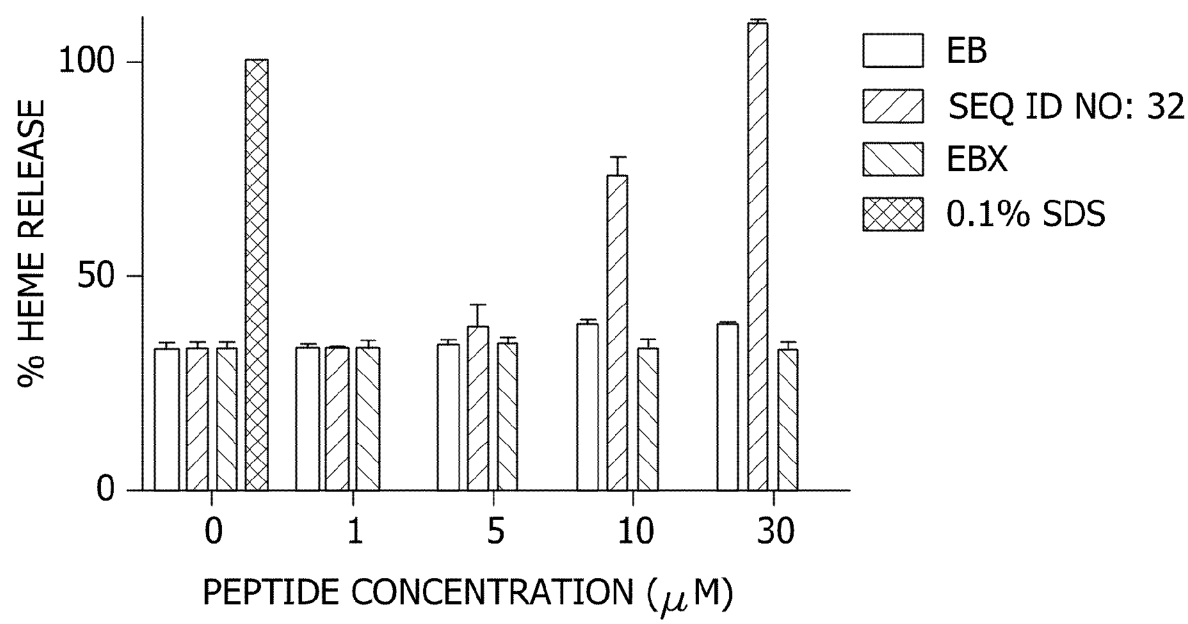
FIG. 4 is a chart depicting the percent of hemoglobin release from cRBCs treated with either 0 μM, 1 μM, 5 μM, 10 μM or 30 μM of EB, EBX, or SEQ ID NO: 32, or 0.1% SDS, as discussed in Example 4.

A 0.5% solution of cRBCs was treated with either 0 μM, 1 μM, 5 μM, 10 μM, or 30 μM of EB, EBX, or the SEQ ID NO: 32 peptide, and the ability of the peptide to compromise the lipid membrane was measured by the release of hemoglobin into the supernatant, as described above. As a positive control for lysis, cells were treated with 0.1% SDS. The results are shown in FIG. 4. Results represent the means of three independent experiments.

As can be seen from FIG. 4, PBS alone and the EB and EBX peptides had no effect on cRBC membrane integrity at any concentration. Conversely, pre-treatment with the SEQ ID NO: 32 peptide induced hemoglobin release at concentrations exceeding 5 μM, with 71% and 100% lysis achieved at 10 μM and 30 μM, respectively, as compared to SDS treated control samples.

These results confirm that EB aggregates influenza virus, and leaves the virion structure intact within these clusters. In contrast, treatment with SEQ ID NO: 32 peptide induces aggregates of structurally disrupted virions. The ability of SEQ ID NO: 32 to disrupt lipid membranes is likely the cause of virion disruption, suggestion that the SEQ ID NO: 32 peptide may be virucidal, a mechanism distinct from full length EB peptide.

Example 5

In this example, the mechanism by which EB induces influenza virus aggregation was evaluated. Specifically, to test whether the interaction between EB and HA triggers a change in the conformation of HA, leading to HA insertion into adjacent virion membranes and viral aggregation, a trypsin protection assay was performed, as described above.

In its native conformation, the HA protein is resistant to proteolytic digestion by trypsin. Once induced to undergo a conformation change like that occurring under low pH conditions, either one or both of the subunits of HA will be cleaved by trypsin.

Purified virion HA (Tk/Wi H5N1) was incubated with PBS, pretreated with either EB, EBX, or SEQ ID NO: 32 at concentrations of either 10 μM or 30 μM, as described above, or acidified to pH 5.0 to induce the fusion conformation change (positive control). All samples were then treated with 5 μg TPCK-trypsin for 1 hour at 37° C., resolved by SDS-PAGE, and HA digestion visualized by Coomassie staining. The results are shown in FIG. 5.

Figure 5:
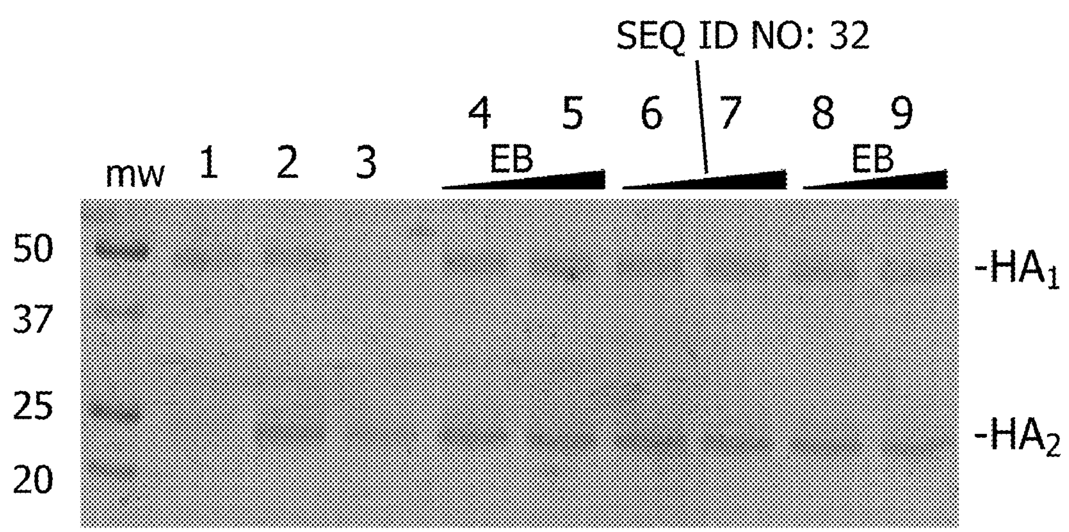
FIG. 5 is a picture of an SDS-PAGE gel of purified HA incubated with varying concentrations of peptide, or acidified with sodium citrate followed by neutralization and addition of TPCK-trypsin, as described in Example 5. Lane 1 is HA alone; lane 2 is HA plus trypsin, with no acidification; lane 3 is acidified HA plus trypsin; lanes 4 and 5 are 10 or 30 μM, respectively, EB-treated HA plus trypsin; lanes 6 and 7 are 10 μM or 30 μM, respectively, SEQ ID NO: 32-treated HA plus trypsin; and lanes 8 and 9 are 10 μM or 30 μM, respectively, EBX-treated HA plus trypsin.

As can be seen from FIG. 5, upon acidification, the $HA_1$ subunit at 50 kDa was completely digested by trypsin (lane 3). In contrast EB (lanes 4 and 5), EBX (lanes 8 and 9), and SEQ ID NO: 32 (lanes 6 and 7) peptide-treated HA remained trypsin-resistant, similar to PBS treated HA with and without trypsin (lanes 1 and 2, respectively). This suggests that the peptides do not induce a major conformation change in HA similar to acidification.

Example 6

In this example, various modifications were made to the SEQ ID NO: 22 peptide, the minimal sequence derivative of EB that retained antiviral activity against influenza virus as determined in Example 1, and the resulting peptides were screened for anti-influenza virus activity. The sequence of each peptide is shown in Table 4.

Figure 7:
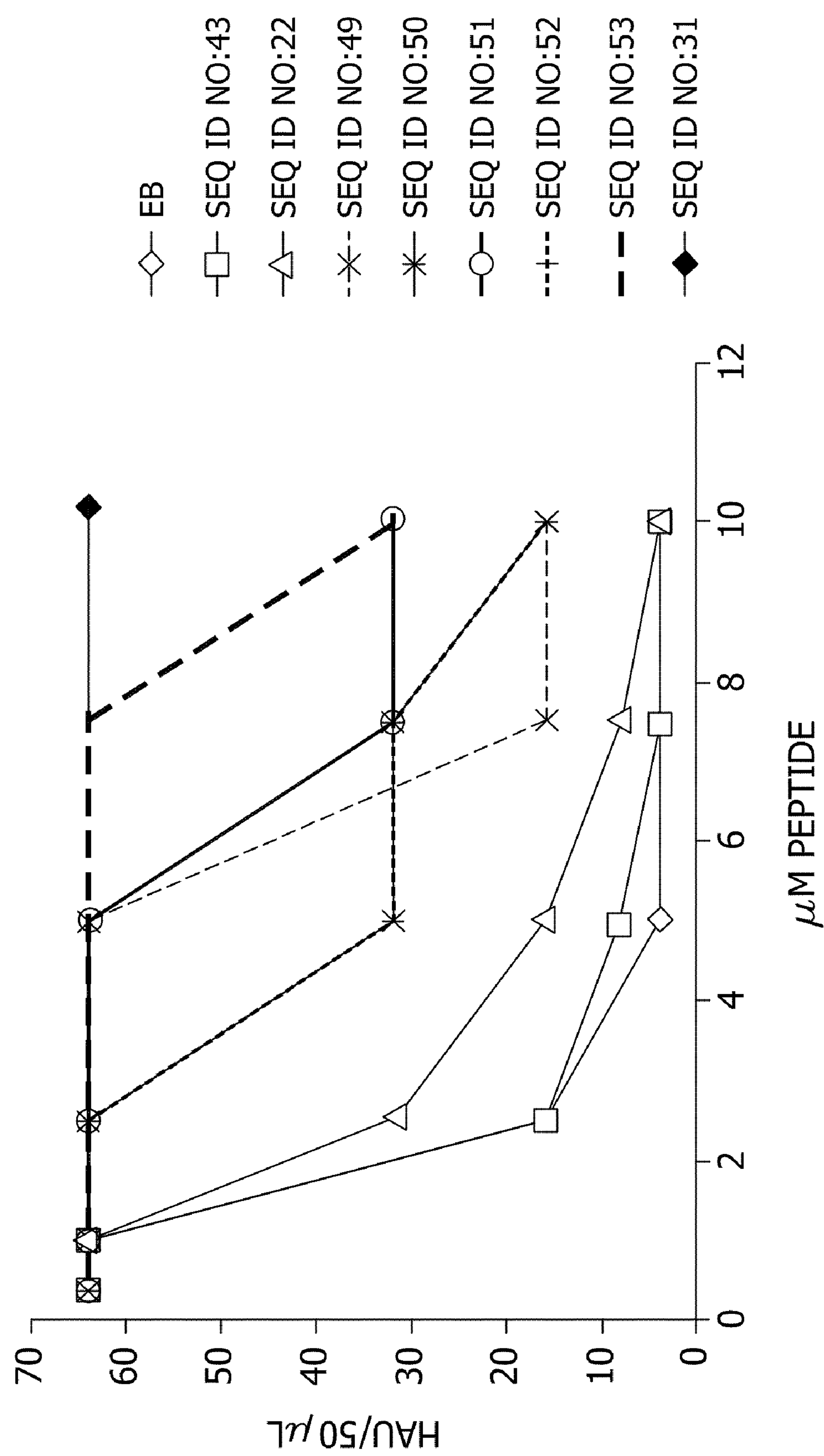
FIG. 7 is a chart showing the results from a hemagglutination assay using various peptides, as discussed in Example 6.

Each peptide was screened for the ability to inhibit viral hemagglutination using the technique described in Example 1, except the HA titer was compared back to virus treated with 10 μM of the EB peptide (considered 100% inhibition). The EB, SEQ ID NO: 22, and EBX peptides were also tested as controls. The results are shown in Table 4. A hemagglutination assay was also performed on some of the peptide, using the procedure set forth in the Test Methods. The results are shown in FIG. 7.

The $EC_{50}$ values were also determined for some active peptides as described above. The results are shown in Table 4.

TABLE 4

| Peptide | Modification | Sequence | %[a] inhibition | $EC_{50}$ (μM) |
|---|---|---|---|---|
| EB (SEQ. ID. NO: 1) | n/a | RRKKAAVALLPAVLLALLAP | 100% | 2 |
| SEQ ID NO: 22 | EB, -5N | RRKKLPAVLLALLAP | 100% | 3 |
| SEQ ID NO: 45 | EB, -5N, no prolines | RRKKLAVLLALLA | 100% | 3 |
| SEQ ID NO: 49 | A substitution | RRKKAAAAAAAAA | 87.5% | ~7 |
| SEQ ID NO: 50 | R removed from N-terminus of SEQ ID NO: 45 | RKKLAVLLALLA | 75% | 8 |
| SEQ ID NO: 51 | RK and L removed from SEQ ID NO: 45 | RKAVLLALLA | 50% | |
| SEQ ID NO: 52 | RRK removed from N-terminus of SEQ ID NO: 45 | KLAVLLALLA | 25% | |
| SEQ ID NO: 53 | RR removed from N-terminus of SEQ ID NO: 45 | KKLAVLLALLA | 0% | |
| SEQ ID NO: 54 | EEDD (SEQ ID NO: 61) substituted for RRKK at N-terminus of SEQ ID NO: 45 | EEDDLAVLLALLA | 0% | |
| SEQ ID NO: 55 | A substituted for L at positions 8 and 9 in SEQ ID NO: 45 | RRKKLAVAAALLA | 0% | |
| SEQ ID NO: 56 | A substituted for L at positions 11 and 12 in SEQ ID NO: 45 | RRKKLAVLLAAAA | 0% | |

TABLE 4-continued

| Peptide | Modification | Sequence | %[a] inhibition | $EC_{50}$ (μM) |
|---|---|---|---|---|
| EBX (SEQ ID NO: 31) | Scrambled EB | RRKKLAALPLVLAAPLAVLA | 0% | |

[a]Hemagglutinating units of an EB-treated sample (10 μM EB) of virus (64 HAU) were reported as 100% and all values were normalized to this and expressed as percent inhibition. Results are indicative of 2-4 independent screens.

As can be seen from Table 4, the derivatives SEQ ID NOs: 45 and 49-51 exhibited antiviral activity, with SEQ ID NO: 45 exhibiting inhibition comparable to that of SEQ ID NO: 22 and the EB peptide (i.e., 100% inhibition as compared to EB-treated). These results demonstrate that the two proline residues in SEQ ID NO: 22 were dispensable for antiviral activity. Additionally, substituting alanine for all residues in SEQ ID NO: 45 except the RRKK (SEQ ID NO: 17) solubility tag resulted in a slight drop in the level of activity (i.e., 87.5% inhibition, as compared to EB-treated). These results suggest that the dileucine repeats in SEQ ID NO: 45 and other antiviral peptides of the present disclosure may be involved in conferring antiviral activity.

As can be seen from FIG. 7, viral hemagglutination activity for SEQ ID NO: 22 was the same as that for the EB peptide at a concentration of 10 μM. Activity was also detected to a lesser extent for SEQ ID NOs: 49, 50, and 51 at 10 μM concentration.

Example 7

In this example, the region of the hemagglutinin (HA) protein where the EB peptide and its derivatives associate to inhibit viral attachment to cells was identified.

An EB inhibition assay was performed as described in the Test Methods section. Briefly, concentrations of 1 μM, 3 μM 7.5 μM or 15 μM of various overlapping VN/1203 HA peptides (obtained from the NIH Biodefense and Engineering Infectious Research Resources Repository (NR-2704, NIAID, NIH) were incubated with or without 2.5 μM of the EB peptide (SEQ ID NO: 1) for 1 hour at 37° C. PR/8 virus (64 HAU) was then added to each reaction and the reactions were incubated an additional hour at 37° C. Two-fold dilutions of each reaction were incubated with 0.5% CRBC for 45 minutes at room temperature. All measures were performed in duplicate.

The results are shown in FIG. 8. The dotted line indicates the normal inhibition of PR/8 by 2.5 μM of the EB peptide. The amino acid residues for the overlapping HA peptides tested are shown along the x-axis. As can be seen from these results, HA peptides spanning amino acids 374-453 competitively inhibited the antiviral activity of EB. Without wishing to be bound to any particular theory, it is believed that these HA peptides bind to the EB peptide directly, thus interfering with the ability of the EB peptide to bind to HA.

The HA peptides spanning amino acids 374-453 of the VN/1203 HA protein were compared to various sequences from additional influenza A viruses. The results are shown in FIG. 9. Shading and dots indicate similar (light shading) and identical (dark shading) residues. As can be seen from these results, the HA peptides spanning amino acids 374-453 of the VN/1203 HA protein are highly conserved among other influenza A viruses, including seasonal influenza strains, avian influenza strains, and swine influenza (H1N1) viruses. These results indicate that the antiviral peptides of the present disclosure may exhibit antiviral activity against a variety of strains of influenza, including avian, seasonal, and swine influenza.

Example 8

In this example, the ability of the SEQ ID NO: 45 peptide to inhibit the attachment of influenza virus to host cells through peptide-mediated aggregation of the influenza virion was evaluated.

To begin, purified PR/8 virus (512 HA units) was treated with PBS (mock) or 2 mM of disuccinimidyl suberate (DSS) (a positive control for the induction of aggregation), or 10 μM of either EB or EBX, or 28 μM of SEQ ID NO: 45 for 1 hour at 37° C., and analyzed by electron microscopy, as described above. The results are representative of 2 to 4 independent studies. The results are shown in FIG. 10.

Figure 10A:
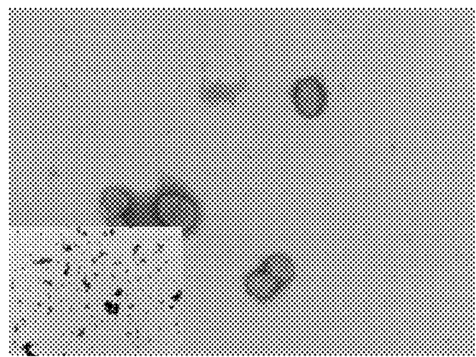
FIG. 10 is a picture from an electron microscope of PR/8 virons that were mock treated (PBS-0 μM peptide) (FIG. 10A) or treated with 2 μM DSS (FIG. 10B), 10 μM EB peptide (FIG. 10C), 10 μM EBX peptide (FIG. 10D), or 28 μM of the SEQ ID NO: 45 peptide (FIG. 10E), as described in Example 8. The FIG. 10A picture was taken at a magnification of 66,000× (inset picture at 25,000×); the FIG. 10B picture was taken at a magnification of 53,000× (inset picture at 7,100×); the FIG. 10C picture was taken at a magnification of 14,000× (inset picture at 5,000×); the FIG. 10D picture was taken at a magnification of 14,000× (inset picture at 5,600×); and the FIG. 10E picture was taken at a magnification of 70,000× (inset picture at 5,000×).
Figure 10B:
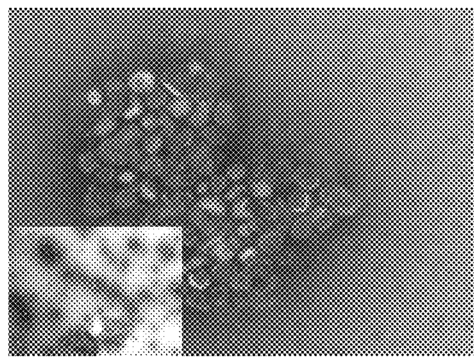
Figure 10C:
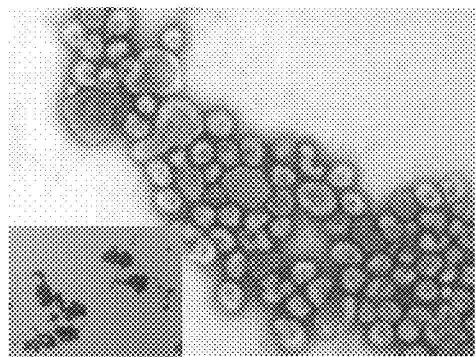
Figure 10D:
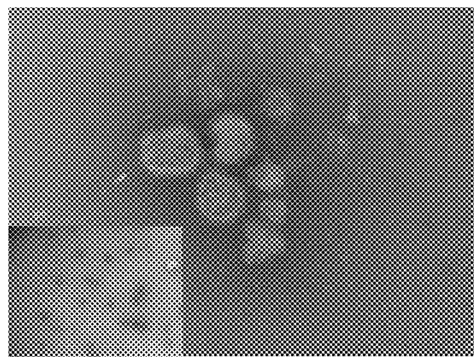
Figure 10E:
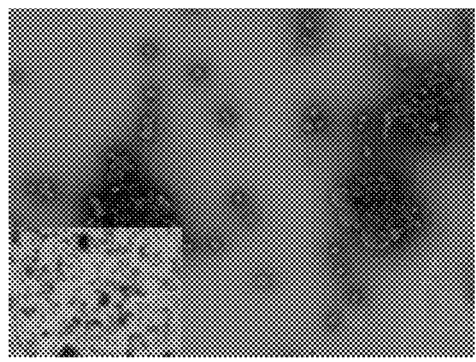

In mock treated (FIG. 10A) and control EBX peptide-treated samples (FIG. 10D), individual virions were uniformly scattered across the field, with sporadic aggregates noted. In contrast, nearly all of the virions treated with full length EB peptide were found in large clusters of individual viral particles, confirming that EB peptide aggregates influenza virus (FIG. 10C). PR/8 virus treated with SEQ ID NO: 45 and DSS was also found in large aggregates with a few individual virions observable in any field, as can be seen in FIGS. 10E and 10B, respectively.

Example 9

In this example, the mechanism by which EB induces influenza virus aggregation was evaluated.

Neuraminidase (NA) inhibition has been implicated in reducing aggregation of virions in solution, in addition to reducing aggregation of budding viruses at the cell surface. To test whether EB-induced viral aggregation is the result of NA inhibition, a neuraminidase activity assay was performed.

Figure 11:
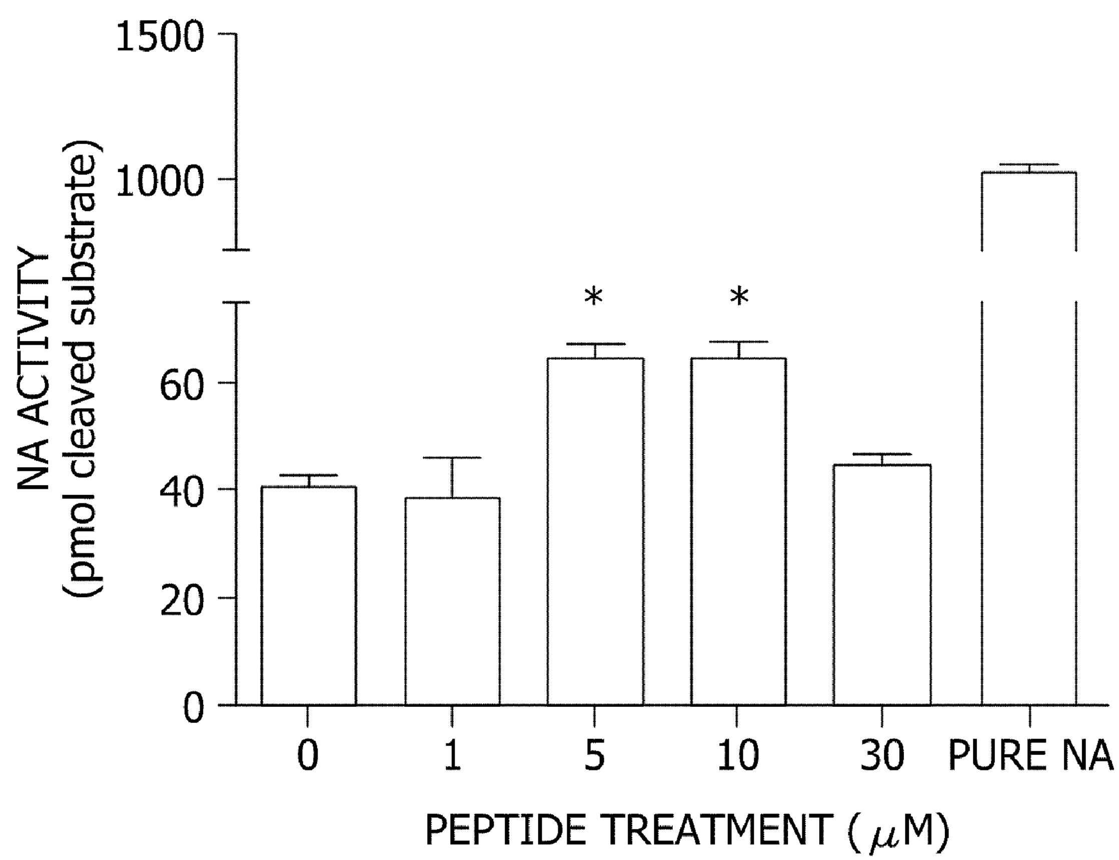
FIG. 11 is a chart showing the results of a neuraminidase activity assay, discussed in Example 9. (*) represents $p<0.05$.

PR/8 virus (64 HAU) was mock treated (0 μM peptide) or treated with either 1 μM, 5 μM, 10 μM, or 30 μM of the EB peptide for one hour at 37° C., followed by incubation on the fluorogenic substrate 2'-(4-methylumbelliferyl)-α-D-N-acetyneuraminic acid (MUNANA) (available from Sigma-Aldrich, St. Louis, Mo.). Purified bacterial NA was used as a positive control (Sigma-Aldrich, St. Louis, Mo.). Fluorescence was measured using a fluorometer with an excitation and emission wavelengths of 365 nm and 450 nm, respectively. The fluorescence measurements were compared to a standard curve of 4-methyl-umberlliferon. The results are shown in FIG. 11, and are expressed as pmol of substrate cleaved by NA per hour. The results represent the mean of triplicate measurements. As can be seen from FIG. 11, the EB peptide did not inhibit NA activity.

When introducing elements of the present disclosure or the preferred embodiments(s) thereof, the articles “a”, “an”, “the” and “said” are intended to mean that there are one or more of the elements. The terms “comprising”, “including”

and "having" are intended to be inclusive and mean that there may be additional elements other than the listed elements.

In view of the above, it will be seen that the several objects of the disclosure are achieved and other advantageous results attained.

As various changes could be made in the above compositions and products without departing from the scope of the disclosure, it is intended that all matter contained in the above description shall be interpreted as illustrative and not in a limiting sense.

What is claimed is:

1. An antiviral peptide selected from the group consisting of SEQ ID NO: 32, SEQ ID NO: 43, and SEQ ID NO: 45.

2. The antiviral peptide of claim 1, wherein the antiviral peptide is selected from the group consisting of SEQ ID NO: 32 and SEQ ID NO: 45.

3. A composition comprising one or more peptide selected from the group consisting of SEQ ID NO: 32, SEQ ID NO: 43, and SEQ ID NO: 45, and a pharmaceutically acceptable carrier.

4. The composition of claim 3, wherein the peptide is selected from the group consisting of SEQ ID NO: 32 and SEQ ID NO: 45.

5. A method of treating or inhibiting an influenza A virus infection in a mammal, the method comprising administering to the mammal an effective amount of an antiviral peptide selected from the group consisting of SEQ ID NO: 32, SEQ ID NO: 43 and SEQ ID NO: 45.

6. The method of claim 5 wherein the antiviral peptide is administered with a pharmaceutically acceptable carrier.

7. The method of claim 5 wherein the antiviral peptide is administered through parenteral administration.

8. The method of claim 5 wherein the antiviral peptide is administered intranasally.

9. The method of claim 5 wherein the antiviral peptide is administered prophylactally.

10. The method of claim 5 wherein the antiviral peptide is administered after the mammal has been exposed to influenza A virus.

11. The method of claim 5 wherein the antiviral peptide is administered at about the time the mammal is exposed to influenza A virus.

* * * * *